US012702788B2

(12) United States Patent
Zou et al.

(10) Patent No.: US 12,702,788 B2
(45) Date of Patent: Aug. 11, 2026

(54) DETACHABLE ESSENTIAL OIL ATOMIZER HEAD AND AROMATHERAPY ATOMIZER

(71) Applicant: Shenzhen Jingxintai Houseware Co., Ltd., Guangdong (CN)

(72) Inventors: Jinshan Zou, Guangdong (CN); Aiqun Lin, Guangdong (CN)

(73) Assignee: SHENZHEN JINGXINTAI HOUSEWARE CO., LTD., Shenzhen (CN)

( * ) Notice: Subject to any disclaimer, the term of this patent is extended or adjusted under 35 U.S.C. 154(b) by 0 days.

(21) Appl. No.: 18/015,195

(22) PCT Filed: Aug. 16, 2022

(86) PCT No.: PCT/CN2022/112767
§ 371 (c)(1),
(2) Date: Jan. 9, 2023

(87) PCT Pub. No.: WO2024/036478
PCT Pub. Date: Feb. 22, 2024

(65) Prior Publication Data
US 2024/0238554 A1 Jul. 18, 2024

(51) Int. Cl.
*A61M 21/02* (2006.01)
*A61M 11/04* (2006.01)
(Continued)

(52) U.S. Cl.
CPC .......... *A61M 21/02* (2013.01); *A61M 11/042* (2014.02); *F24F 8/50* (2021.01);
(Continued)

(58) Field of Classification Search
CPC .... A61M 2021/0016; A61M 2205/127; A61M 2205/8206; A61M 11/042; A61M 11/00; A61L 9/14; A61L 2209/134; F24F 8/50
(Continued)

(56) References Cited

U.S. PATENT DOCUMENTS 7,878,418 B2 * 2/2011 Sevy .................... B05B 7/2416
128/200.18
9,511,166 B1 * 12/2016 Li ........................ B05B 7/2416
(Continued)

FOREIGN PATENT DOCUMENTS

CN 104524617 A 4/2015
CN 215523671 U 1/2022
(Continued)

OTHER PUBLICATIONS

International Search Report dated Apr. 20, 2023; International Application No. PCT/CN2022/112767; 4 pages (non-English).

*Primary Examiner* — Jennifer Robertson
*Assistant Examiner* — Brogan R Landeen
(74) *Attorney, Agent, or Firm* — CANTOR COLBURN LLP

(57) ABSTRACT

A detachable essential oil atomizer head and an aromatherapy atomizer are provided. The detachable essential oil atomizer head includes: a bottom shell, a shell cover, a connection part and an atomization structure, the shell cover is covered on the bottom shell and encloses the bottom shell so as to form an accommodation space, the shell cover is provided with an air outlet communicated with the accommodation space, an essential oil bottle is arranged on one side of the connection part, the other side of the connection part away from the essential oil bottle is detachably connected with the bottom shell, the bottom shell is provided with an insertion hole communicated with the accommodation space. The atomization structure includes a ceramic atomization plate and a flexible wick, the ceramic atomization plate is mounted in the accommodation space. According to the present application, a portable aromatherapy atomizer is realized.

14 Claims, 18 Drawing Sheets

(51) Int. Cl.
*A61M 21/00* (2006.01)
*F24F 8/50* (2021.01)

(52) U.S. Cl.
CPC ............... *A61M 2021/0016* (2013.01); *A61M 2205/0288* (2013.01); *A61M 2205/121* (2013.01); *A61M 2205/127* (2013.01); *A61M 2205/14* (2013.01); *A61M 2205/3317* (2013.01); *A61M 2205/8206* (2013.01)

(58) Field of Classification Search
USPC ......................... 239/44, 135, 34, 55, 71, 99; 261/DIG. 88, 30, DIG. 89, 78.1
See application file for complete search history.

(56) References Cited

U.S. PATENT DOCUMENTS

| | | | | |
|---|---|---|---|---|
| 11,197,941 | B1 * | 12/2021 | Gao | B05B 7/0012 |
| 2017/0157281 | A1 * | 6/2017 | Ma | A61L 9/14 |
| 2022/0168538 | A1 | 6/2022 | Liu | |

FOREIGN PATENT DOCUMENTS

| | | | | | |
|---|---|---|---|---|---|
| CN | 215584943 | U | * | 1/2022 | |
| CN | 215938435 | U | * | 3/2022 | |
| CN | 216536317 | U | | 5/2022 | |
| CN | 114732932 | A | | 7/2022 | |
| CN | 217796977 | U | * | 11/2022 | B05B 17/0684 |
| DE | 202013102215 | U1 | * | 7/2013 | A61L 9/14 |
| WO | WO-2020063055 | A1 | * | 4/2020 | A61L 9/14 |
| WO | WO-2022169314 | A2 | * | 8/2022 | A24F 40/51 |

* cited by examiner

DETACHABLE ESSENTIAL OIL ATOMIZER HEAD AND AROMATHERAPY ATOMIZER

CROSS-REFERENCE TO RELATED APPLICATIONS

The present application is a 35 U.S.C. § 371 national stage application of PCT international patent application No. PCT/CN2022/112767, filed on Aug. 16, 2022, the entire contents of which are incorporated herein by reference.

FIELD

The present application relates to the technical field of aromatherapy devices, and more particularly to a detachable essential oil atomizer head and an aromatherapy atomizer.

BACKGROUND

Regarding the existing atomization devices, especially the atomization devices for aromatherapy, some of the atomization devices are pump-air type atomization devices using air pumps, and some of the atomization devices are atomization plate type atomization devices which realizes atomization through oscillation of a micro-pore atomization plate (the micro-hole atomization plate includes a steel piece piercing through the micro-pore, and an outer layer of the steel piece is a ceramic vibration piece).

The existing pump-air type atomization device uses an air pump to pump air, so that the airflow forms a high-speed airflow through a small hole, essential oil in an essential oil bottle is sucked out by a negative pressure and is atomized. Then, the air mixed with the atomized essential oil flows out, thereby achieving the purpose of spreading the essential oil into the air to realize aromatherapy. However, since this pump air atomization device uses the air pump as its power source, thus, this pump air type atomization device has a large size, and it is inconvenient to carry around this pump air type atomization device.

SUMMARY

One objective of the present application is to provide a detachable essential oil atomizer head and an aromatherapy atomizer, which aims to solve a problem on how to realize a portable aromatherapy atomizer.

In order to achieve the objective, the technical solutions used in the embodiments of the present application are as follows:

In the first aspect, a detachable essential oil atomizer head is provided, the detachable essential oil atomizer head includes a bottom shell, a shell cover, a connection part and an atomization structure. The shell cover is covered on the bottom shell and encloses the bottom shell to form an accommodation space, the shell cover is provided with an air outlet communicated with the accommodation space, an essential oil bottle is mounted at one side of the connection part, the other side of the connection part away from the essential oil bottle is detachably connected to the bottom shell. The bottom shell is provided with an insertion hole communicated with the accommodation space. The atomization structure includes a ceramic atomization plate and a flexible wick, the ceramic atomization plate is mounted in the accommodation space, one end of the flexible wick is arranged on one side of the connection part away from the essential oil bottle and abuts against the ceramic atomization plate, the other end of the flexible wick penetrates through the connection part and is extended into the essential oil bottle. The flexible wick is provided with at least one spray-through hole.

In one embodiment, the connection part includes a connection body and a support frame, the support frame is provided with an atomization chamber, an outlet hole and an oscillation avoidance hole, both the outlet hole and the oscillation avoidance hole are communicated with the atomization chamber. The support frame are arranged to be inserted in the connection body, the flexible wick encloses the support frame to cover the oscillation avoidance hole and is kept away from the outlet hole, and the flexible wick is arranged to penetrate through the support frame and the connection body and is extended into the essential oil bottle. The support frame penetrates through the insertion hole and is inserted into the accommodation space, such that a part of the flexible wick corresponding to the oscillation avoidance hole abuts against the ceramic atomization plate, and the outlet hole is communicated with the air outlet. The connection body is detachably connected with the bottom shell.

In one embodiment, the connecting part further includes a support spring assembled in the atomization chamber. One end of the support spring is arranged in an inner wall of the atomization chamber, the other end of the support spring penetrates through the oscillation avoidance hole and is pressed against the flexible wick.

In one embodiment, a middle part of a position of the flexible wick abutting against the ceramic atomization plate is provided with the spray through-hole, and the spray through-hole has an aperture ranging from 0.5 mm to 5 mm.

In one embodiment, the detachable essential oil atomizer further includes a support structure fixedly mounted in the accommodation space. The support structure is provided with a cavity communicated with the air outlet, the atomization plate is mounted in the support structure and is located in the cavity.

In one embodiment, the atomization structure further includes a terminal assembly, a terminal adapter, a terminal heat dissipation member and a conductive spring, the terminal assembly includes a first terminal and a second terminal, both the terminal adapter and the terminal heat dissipation member are mounted in the support structure. One end of the conductive spring is electrically connected with the terminal adapter, the other end of the conductive spring abuts against the ceramic atomization plate to enable the ceramic atomization plate to be conductive. The terminal heat dissipation member encloses and supports the ceramic atomization plate, and the terminal heat dissipation member is electrically connected with the ceramic atomization plate. The first terminal is electrically connected to the terminal adapter, the second terminal is electrically connected with the terminal heat dissipation member, and the first terminal and the second terminal are configured to be electrically connected to a power supply.

In one embodiment, the atomization structure further includes a silicone sleeve, one end of the silicone sleeve abuts against the ceramic atomization plate, the other end of the silicone sleeve abuts against the terminal adapter, and the silicone sleeve is sleeved on the conductive spring.

In one embodiment, the connection part further includes a sealing gasket, the sealing gasket is configured to form a sealing between the connection body and a bottle mouth of the essential oil bottle when the connection part is connected with the essential oil bottle.

According to a second aspect of the present application, an aromatherapy atomizer is provided. In particular, the aromatherapy atomizer includes: a housing, a battery, a circuit board and the aforesaid detachable essential oil atomizer. The housing is provided with an accommodation compartment for accommodating the essential oil bottle, and the bottom shell is detachably connected with the housing. The battery mounted in the accommodation space, the circuit board is mounted in the accommodation space, the battery is electrically connected with the circuit board, both the first terminal and the second terminal are electrically connected with the circuit board.

In one embodiment, the aromatherapy atomizer further includes a fan, the fan is fixedly mounted in the accommodation space and is electrically connected with the circuit board. The support frame is further provided with a gas inlet communicated with the atomization chamber, and the gas inlet is opposite to the fan when the support frame penetrates through the insertion hole and is inserted into the accommodation space.

According to a third aspect of the present application, an aromatherapy atomizer is provided. In particular, the aromatherapy atomizer includes: a housing, a battery, a circuit board, a contact member and the aforesaid detachable essential oil atomizer. The housing is provided with a mounting space and an accommodation compartment for accommodating the essential oil bottle, and the bottom shell is detachably connected with the housing. Both the battery and the circuit board are mounted in the mounting space, the battery is electrically connected with the circuit board. The contact member is electrically connected with the circuit board, and the contact member pierces through the mounting space. Both the first terminal and the second terminal pierce through the bottom shell, the first terminal and the second terminal are electrically connected with the contact member when the essential oil bottle is inserted into the accommodation compartment.

In one embodiment, the aromatherapy atomizer further includes a fan mounted in the mounting space and electrically connected with the circuit board. The housing is provided with an air outlet, the fan is arranged to be opposite to the air outlet. The bottom shell or the shell cover is further provided with a gas inlet, the support frame is further provided with an air inlet communicated with the atomization chamber. The air inlet is communicated with the gas inlet when the support frame penetrates through the insertion hole and is inserted into the accommodation space, and the gas inlet is communicated with the air outlet when the essential oil bottle is inserted into the accommodation compartment.

In one embodiment, a limiting magnet is arranged in the shell cover, and an adsorption magnet is arranged in the housing. The adsorption magnet is configured to be magnetically connected with the limiting magnet when the essential oil bottle is inserted into the accommodation compartment.

In one embodiment, the connection part is provided with a detection magnet, the aromatherapy atomizer further includes a Hall sensor arranged in the mounting space and electrically connected with the circuit board. The Hall sensor is configured to detect whether the detection magnet is mounted in place when the essential oil bottle is inserted into the accommodation compartment.

The beneficial effects of the detachable essential oil atomizer head according to the embodiments of the present application are described below:

- the atomizer head according to the present application is applied in the aromatherapy atomizer, the atomizer head uses the ceramic atomization plate as the core component for atomizing the aromatherapy essential oil, the size of the atomizer head can be greatly reduced due to the utilizations of the water absorption of the flexible wick and the arrangement of the flexible wick abutting against the ceramic atomization plate, the overall size of the aromatherapy atomizer can be greatly reduced, and it is convenient for a user to carry around the aromatherapy atomizer.

BRIEF DESCRIPTION OF THE DRAWINGS

In order to describe the embodiments of the present application more clearly, a brief introduction regarding the accompanying drawings that need to be used for describing the embodiments or exemplary technologies is given below. It is apparent that the accompanying drawings described below are merely some embodiments of the present application, a person of ordinary skill in the art may also acquire other drawings according to the current drawings without paying creative labor.

DETAILED DESCRIPTION OF THE EMBODIMENTS

Figure 1:
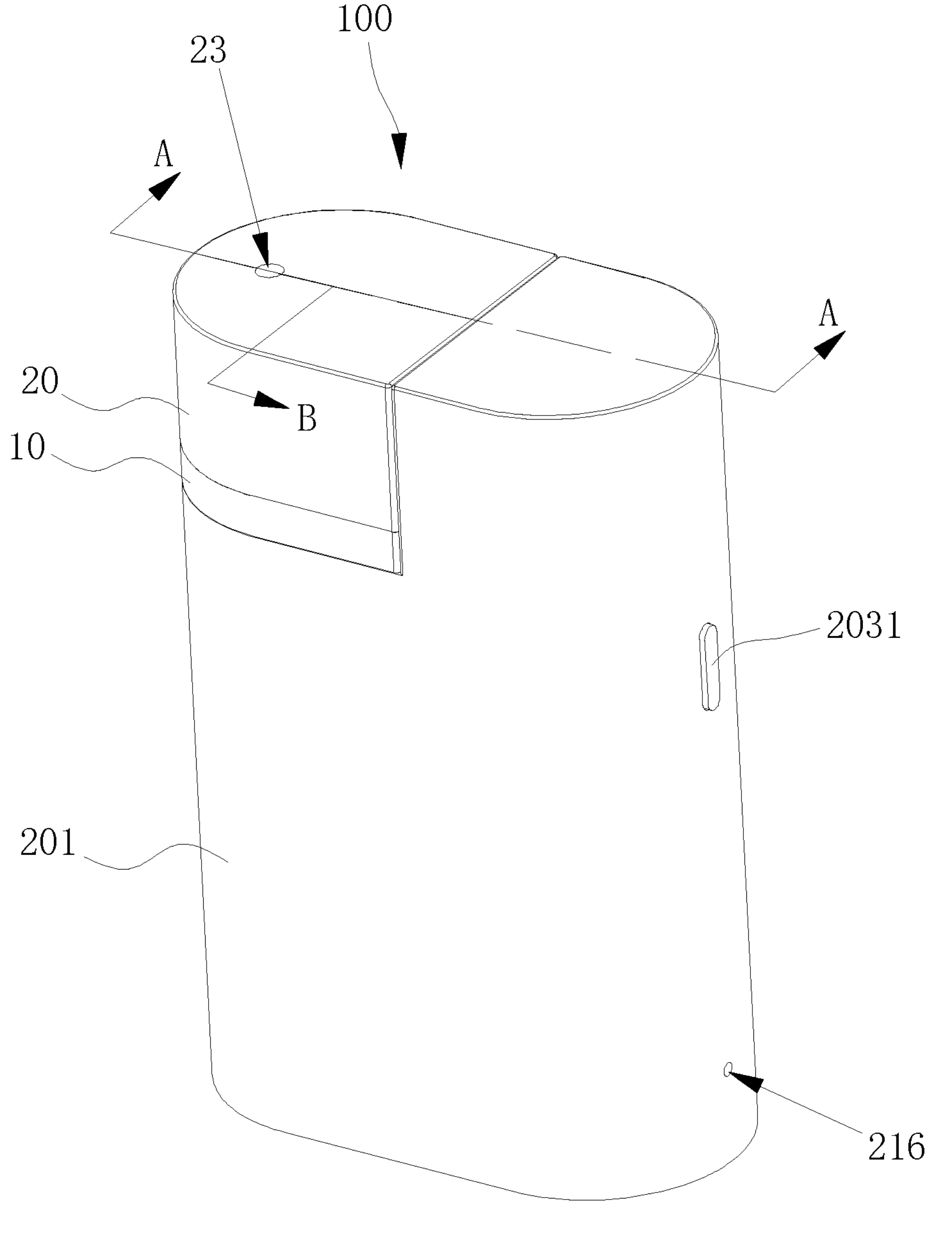
FIG. 1 illustrates schematic assembly diagram of an aromatherapy atomizer according to a first embodiment of the present application.

In order to make the purpose, the technical solution and the advantages of the present application be clearer and more understandable, the present application will be further described in detail below with reference to accompanying figures and embodiments. It should be understood that the embodiments described in detail herein are merely intended to illustrate but not to limit the present application.

It needs to be noted that, when one component is described to be "fixed to" or "arranged on" another component, this component may be directly or indirectly arranged on another component. When it is described that one component "is connected with" the other component, this component may be directly or indirectly connected to the other component. Orientation or position relationships indicated by terms including "upper", "lower", "left" and "right" are based on the orientation or position relationships shown in the accompanying figures and is only used for the convenience of description, instead of indicating or implying that the indicated device or element must have a specific orientation and is constructed and operated in a particular orientation, and thus should not be interpreted as limitation to the present application. For the person of ordinary skill in the art, the specific meanings of the aforesaid terms may be interpreted according to specific conditions. Terms of "the first" and "the second" are only for the purpose of describing conveniently and should not be interpreted as indicating or implying relative importance or implicitly indicating the number of indicated technical features. "Multiple/a plurality of" means two or more unless there is an additional explicit and specific limitation.

In order to describe the technical solutions of the present application, the technical solutions of the present application are described in detail with reference to the accompanying figures and the embodiments.

First Embodiment

As shown in FIGS. 1-12, a schematic structural diagram of an aromatherapy atomizer in the first embodiment of the present application is illustrated.

The aromatherapy atomizer in the first embodiment of the present application can atomize the aromatherapy essential oil so as to aromatize the surrounding air, so that the surrounding air can be mixed with a subtle aroma. Moreover, the aromatherapy atomizer has the characteristics of compactness and portability, and it is convenient for a user to carry around the aromatherapy atomizer, and it is especially convenient for a female user to carry around the aromatherapy atomizer.

In the designing process of the aromatherapy atomizer of the present application, firstly, the atomizer head 100 included in the aromatherapy is innovatively designed. As shown in FIGS. 6-10, the atomizer head 100 includes a bottom shell 10, a shell cover 20, a connection part 11 and an atomization structure 40. The shell cover 20 is covered on one side of the bottom shell 10 away from the connection part 11 (in particular, the shell cover 20 and the bottom shell 10 are locked by screws 65), the shell cover 20 and bottom shell 10 are enclosed to form an accommodation space 21. One side of the bottom shell 10 is provided with the connection part 11 detachably connected with an essential oil bottle 300, and the connection part 11 is detachably connected with the bottom shell 10.

The essential oil bottle 300 is stored with aromatherapy essential oil, the bottom shell 10 or the shell cover 20 is provided with an air inlet 22 and an air outlet 23. Preferably, the shell cover 20 is provided with the air inlet 22 and the air outlet 23. Preferably, the shell cover 20 is provided with the air inlet 22 and the air outlet 22. The bottom shell 10 is provided with an insertion hole communicated with the accommodation space 21. The atomization structure 40 includes a ceramic atomization plate 41 and a flexible wick 50, the ceramic atomization plate 41 is arranged in the accommodation space 21, one end of the flexible wick 50 is arranged on one side of the connection part 11 away from the essential oil bottle 300 to abut against the ceramic atomization plate 41, the other end of the flexible wick 50 penetrates through the connection part 11 and is extended into the essential oil bottle 300. The part of the flexible wick 50 abutting against the ceramic atomization plate 41 is provided with at least one spray through-hole 51.

A high frequency oscillation (oscillation frequency is 1.7 MHz or 2.4 MHz, which extends the range of human hearing, so that the high frequency oscillation is not harmful to human body) is used by the ceramic atomization plate 41, through high frequency oscillation (which is also referred to as high frequency resonance) of the ceramic atomization plate 41, the aromatherapy essential oil in the essential oil bottle 300 is converted into small particles suspended in the air by oscillation, so that natural floating vapor is produced without heating or adding any chemical reagent. Thus, the ceramic atomization plate 41 is used as the core atomization device in the first embodiment of the present application, the size of the atomizer head 100 can be designed to be smaller, and it is convenient for the user to carry around the atomizer head 100.

The atomizer head 100 provided in the present application is applied to the aromatherapy atomizer, the atomizer head 100 uses the ceramic atomization plate 41 as the core component to achieve atomization of the aromatherapy essential oil, and water absorption of the flexible wick 50 and the arrangement of abutting the flexible wick 50 against the ceramic atomization plate 41 are utilized, so that the size of the atomizer head 100 can be greatly reduced, and the overall size of the aromatherapy atomizer is greatly reduced, and it is convenient for the user to carry around the aromatherapy atomizer. Moreover, the connection part 11 can be disassembled from the bottom shell 10, since the connection part 11 and the flexible wick 50 of the atomizer head 100 are assembled into a separate component that can be disassembled from the bottom shell 10. When the user needs to replace the aromatherapy essential oil with a different fragrance, the user can remove the connection part 11 and the essential oil bottle 300 from the bottom shell 10, and then quickly replace the essential oil bottle 300 having the desired fragrance, and replace a new connection part 11 and the flexible wick 50 connected with the essential oil bottle 300.

Figure 9:
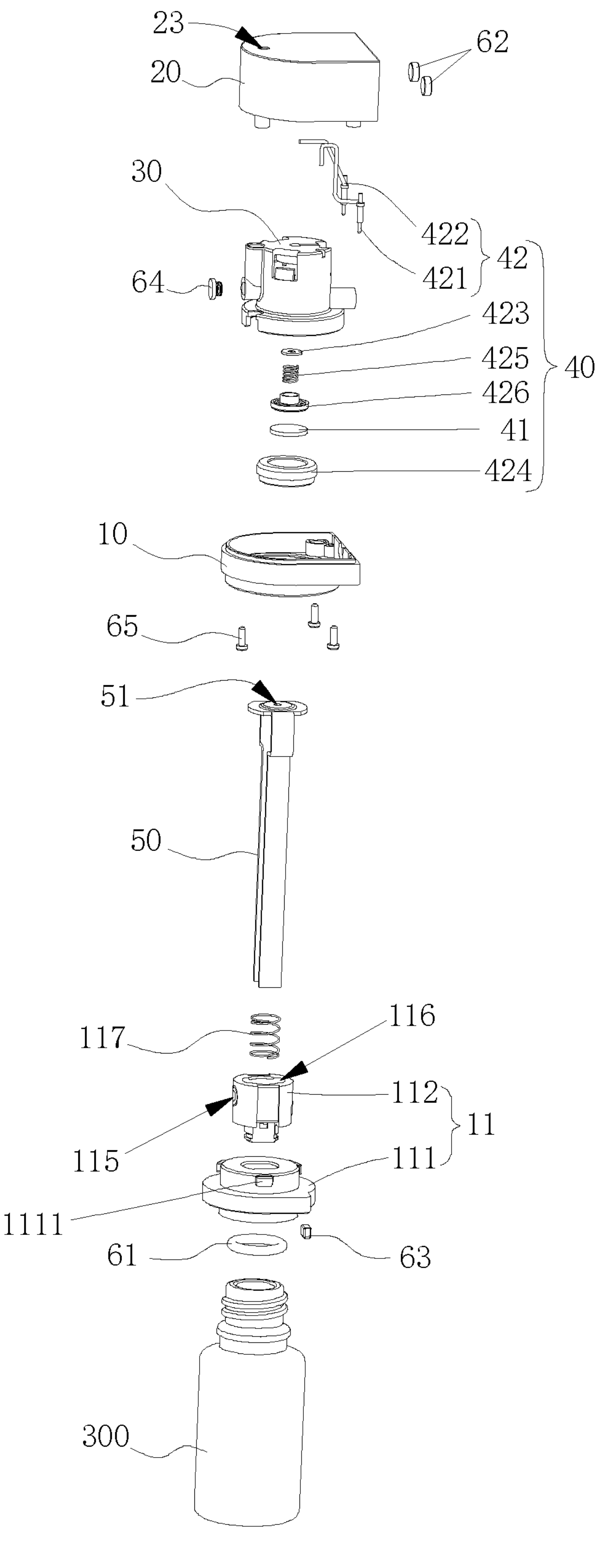
FIG. 9 illustrates a second exploded view of the atomizer head and the essential oil bottle in the aromatherapy atomizer according to the first embodiment of the present application.
Figure 10:
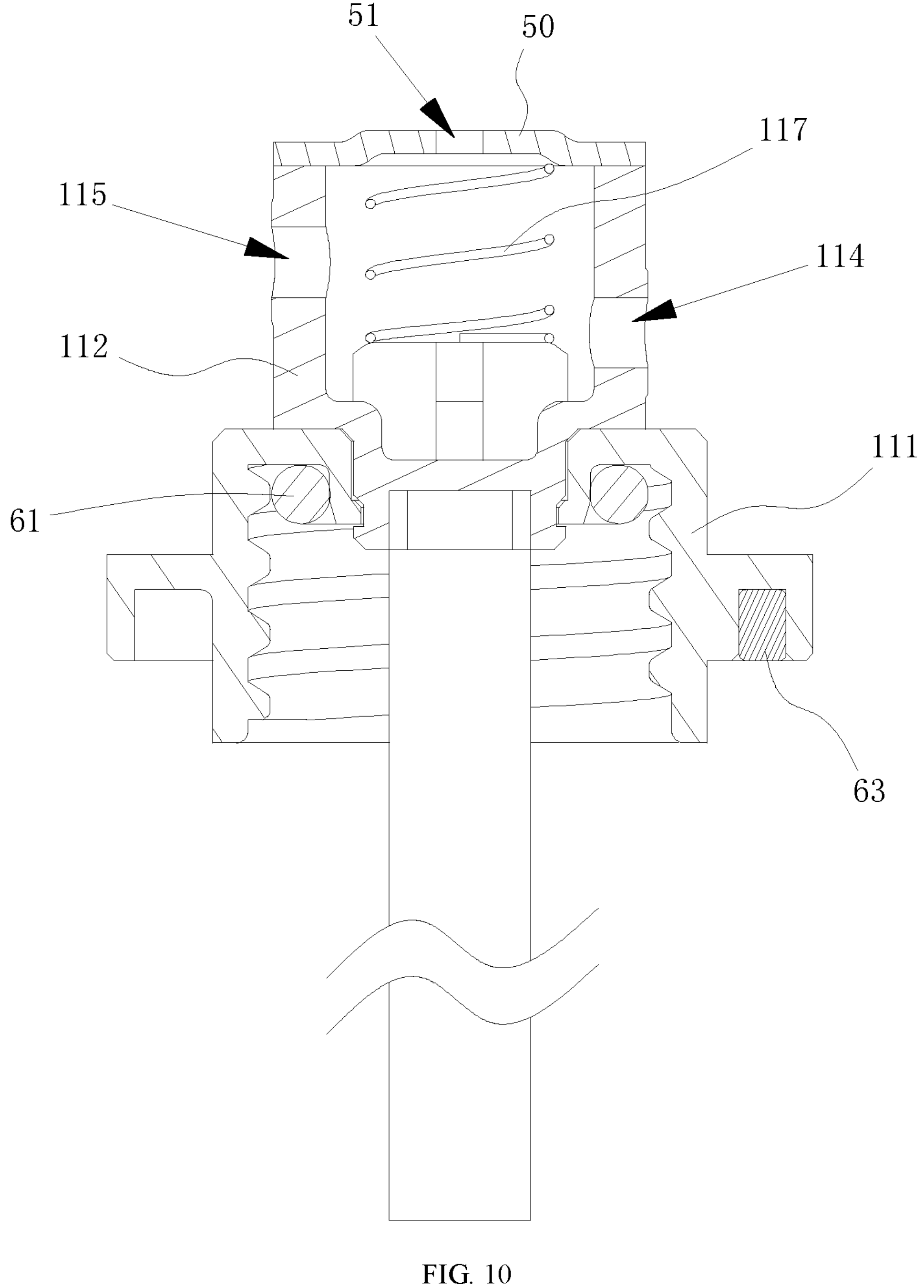
FIG. 10 illustrates a sectional view of the atomizer head in the aromatherapy atomizer according to the first embodiment of the present application.
Figure 11:
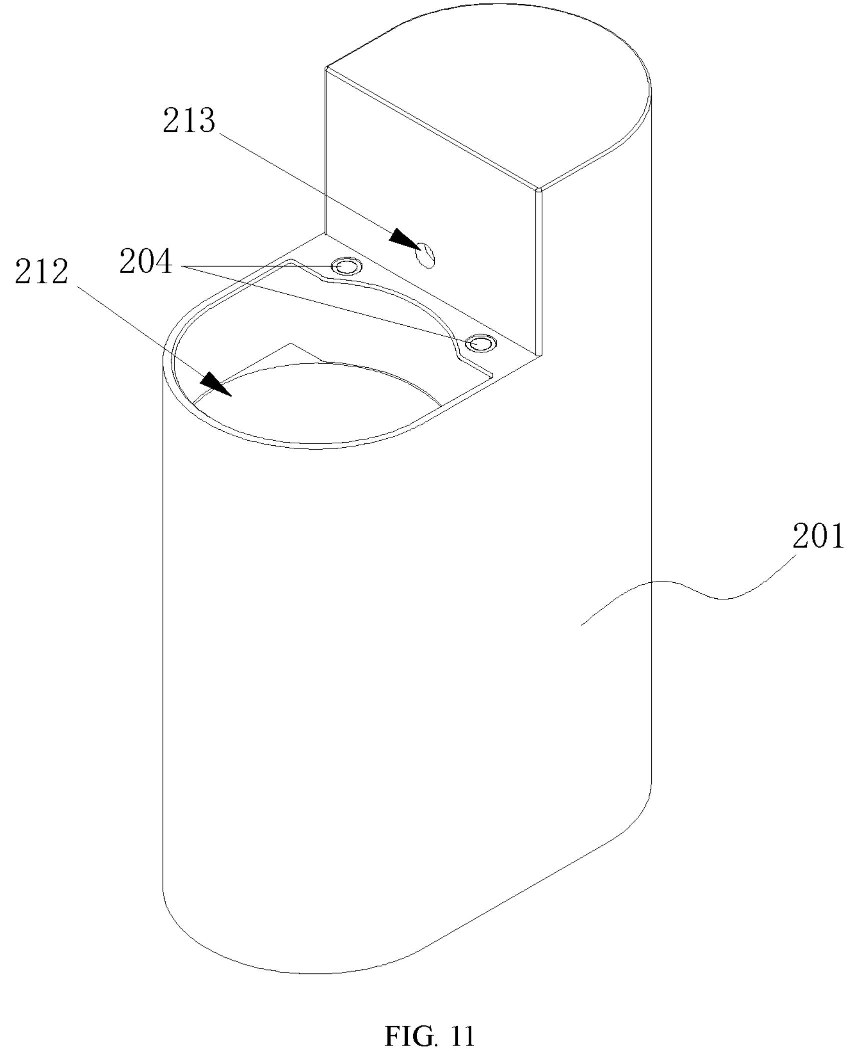
FIG. 11 illustrates a schematic assembly diagram of a housing, a battery, a circuit board and a contact member in the aromatherapy atomizer according to the first embodiment of the present application.

As shown in FIGS. 9 and 10, in the first embodiment of the present application, the connection part 11 includes a connection body 111 and a support frame 112, the support frame 112 is provided with an atomization chamber 113 and an gas inlet 114, an outlet hole 115 and an oscillation avoidance hole 116 communicated with the atomization chamber 113. The flexible wick 50 encloses the support frame 112 and covers the oscillation avoidance hole 116, and the flexible wick 50 is kept away from the gas inlet 114 and the outlet hole 115. The flexible wick 50 penetrates through the support frame 112 and the connection body 111, and is extended into the essential oil bottle 300. In particular, a circumference of the support frame 112 is provided with a convex edge, and the connection body 111 is provided with a clamp groove, and the convex edge snaps into the clamp groove after the support frame 112 is inserted into the connection body 111, so that the support frame 112 is avoided from being separated from the connection body 111. The bottom shell 10 is provided with an insertion hole communicated with the accommodation space 21, and the support frame 112 penetrates through the insertion hole and is inserted into the accommodation space 21, such that the flexible wick 50 abuts against the ceramic atomization plate 41. The gas inlet 114 is communicated with the air inlet 22, the outlet hole 115 is communicated with the air outlet 22, and the connection body 111 is configured to be detachably connected with the essential oil bottle 300 through thread screwing. In this way, the atomizer head 100 in the first embodiment of the present application is designed as a combined structure, either. That is, the connection body 111, the support frame 112 and the flexible wick 50 are assembled into one component, the bottom shell 10, the shell cover 20 and the atomization structure 40 are assembled into one component, then, the two components are assembled into one single component through a dismountable connection between the connection body 111 and the bottom shell 10. Due to this arrangement, the user can enable this component assembled by the connection body 111, the support frame 112 and the flexible wick 50 to be fixedly assembled with the essential oil bottle 300. When multiple essential oil bottles 300 having different fragrances are used, the component assembled by the connection body 111, the support frame 112 and the flexible wick 50 can be fixedly assembled with the essential oil bottles 300, respectively. When the user needs to replace an essential oil bottle 300 with a different fragrant, he/she only needs to simply remove the old component assembled by the connection body 1111, the support frame 112 and the flexible wick 50, and the old essential oil bottle 300 from the component assembled by the bottom shell 10, the shell cover 20 and the atomization structure 40, and replace the old component with the new essential oil bottle 300 and the new component assembled by the connection body 111, the support frame 112 and the flexible wick 50, and connect the new component with the bottom shell 10. Thus, it is convenient for the user to replace the essential oil bottles 300 having different fragrances.

Figure 8:
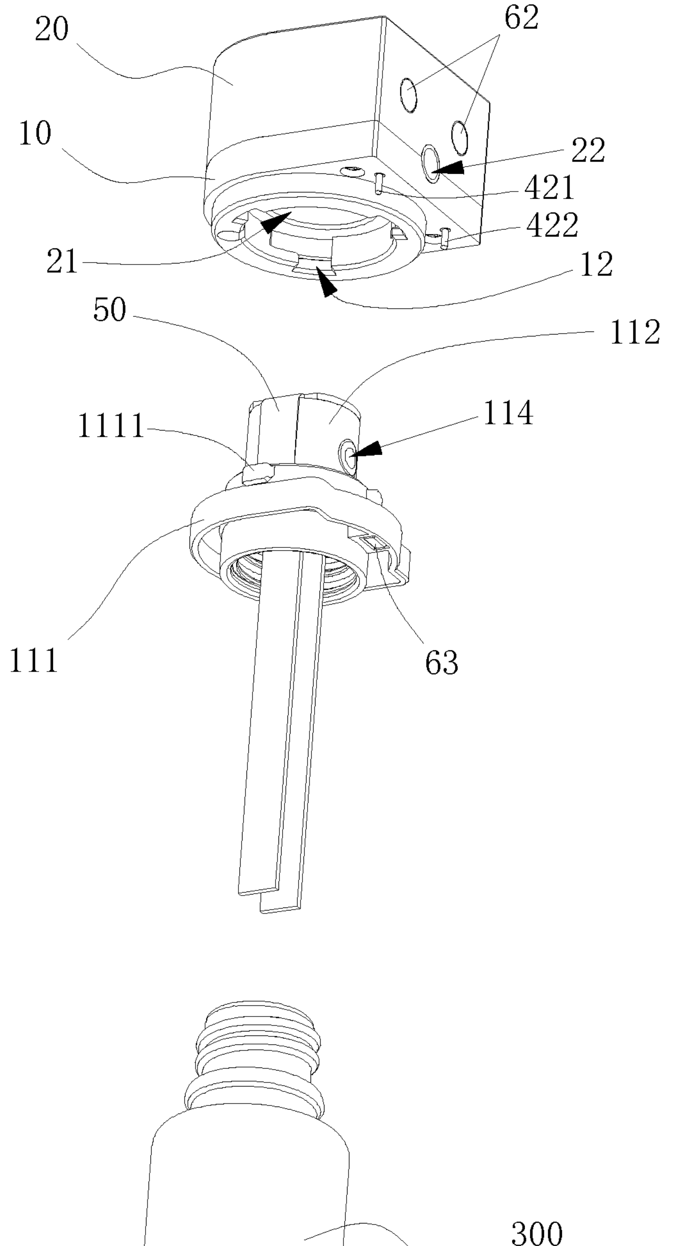
FIG. 8 illustrates a first exploded view of the atomizer head and the essential oil bottle in the aromatherapy atomizer according to the first embodiment of the present application.

As shown in FIG. 8, the connection body 111 is provided with a snap tab 1111, and an inner edge of the insertion hole of the bottom shell 10 is provided with a buckle 12 accordingly, and the snap tab 1111 corresponds to the buckle 12 and enters the insertion hole. Then, the connection body 111 is rotated to achieve a dismountable connection between the connection body 111 and the bottom shell 10. When the connection body 111 needs to be assembled from the bottom shell 10, it only needs to screw the connection body 111 in a reverse direction to realign the snap tab 11111 with the buckle 12, and then pull out the bottom shell 10 to complete the disassembly of the bottom shell 10 and the connection body 111.

As shown in FIG. 2, FIG. 5, FIG. 9 and FIG. 10, the connection part 11 further includes a sealing gasket 61, the sealing gasket 61 is configured to enable the connection part 11 to be sealed with an opening of the essential oil bottle 300, when the connection part 11 is connected to the essential oil bottle 300. In this way, even if the essential oil bottle 300 is tilted during a movement of the atomizer head 100, the liquid in the essential oil bottle 300 will not spill out from the edge of the essential oil bottle 300. Furthermore, the flexible wick 50 penetrates through the support frame 112 and the connection body 111 and extends into the bottle 300 to be immersed in the essential oil. Thus, it is ensured that the flexible wick 50 can absorb oil smoothly through utilization of capillary water absorption and the compressibility of the flexible wick 50, and a condition that air cannot enter the essential oil bottle 300 through small crevices of the flexible wick 50 when the essential oil bottle 300 is upended is avoided simultaneously (in this condition, the air in the bottle 300 is under a slight negative pressure). Thus, the essential oil cannot flow out.

As shown in FIGS. 4, 5, 9 and 10, the connection part 11 further includes a support spring 117, the support spring 117 is mounted in the atomization chamber 113, one end of the support spring 117 is pressed against an inner wall (the bottom wall) of the atomization chamber 113, and the other end of the support spring 117 penetrates through the oscillation avoidance hole 116 and is pressed against the flexible wick 50. The flexible wick 50 that covers the oscillation avoidance hole 116 is always abutted against the ceramic atomization plate 41 through the support spring 117. Thus, it is ensured that the ceramic atomization plate 41 can always be efficiently oscillated to produce vapor, the vapor enters the atomization chamber 113, and then is vented out through the outlet hole 115 and the air outlet 22.

In the first embodiment of the present application, a middle of the part of the flexible wick 50 abutting against the ceramic atomization plate 41 is only provided with one spray through-hole 51, and an aperture diameter of the spray through-hole 51 ranges from 0.5 mm to 5 mm, that is, the aperture diameter of the spray through-hole 51 can be approximately equal to 0.5 mm, or 1.0 mm, or 1.5 mm, or 2 mm, or 2.5 mm, or 3 mm, or 3.5 mm, or 4 mm, or 4.5 mm, or 5 mm. Since the flexible wick 50 can be bent freely, the flexible wick 50 can be bent to fit with the essential oil bottles 300 having various sizes and heights after extending into the essential oil bottle 300, the flexible wick 50 can extend to the bottom of the essential oil bottle 300, so that a dead angle of liquid absorption is avoided, the liquid in the essential oil bottle 300 can be completely absorbed, and a waste of essential oil is avoided. Compared with the use of cotton swabs, the liquid in the essential oil bottle 300 can be used more completely.

As shown in FIGS. 6 to 9, the atomizer head 100 further includes a support structure 30. In particular, when the atomizer head 100 is assembled, the support structure 30 is fixedly mounted in the accommodation space 21. The support structure 30 is provided with a cavity 31 which is communicated with the air inlet 22 and the air outlet 22, so that the vapor can be output in a target direction. The main body of the support structure 30 in the first embodiment is integrally shaped through injection molding; moreover, the cavity 31 and the channels respectively communicated with the air inlet 22 and air outlet 22 are molded through the core, as shown in FIG. 9. In order to vent out vapor upwards (when the atomizer 100 is upright, the atomizer 100 vents outs vapor upwards), the channel communicated with the air outlet 23 is designed as a right-angle channel. In order to facilitate pulling out the core of the horizontal section and the core of the vertical section in the right-angle channel after the injection molding, the horizontal section is arranged to be away from the cavity 31 and form an opening which is blocked by a plug 64, so that the vapor cannot flow out of the opening in a venting process, and thus can vent out from the air outlet 23 completely.

Figure 4:
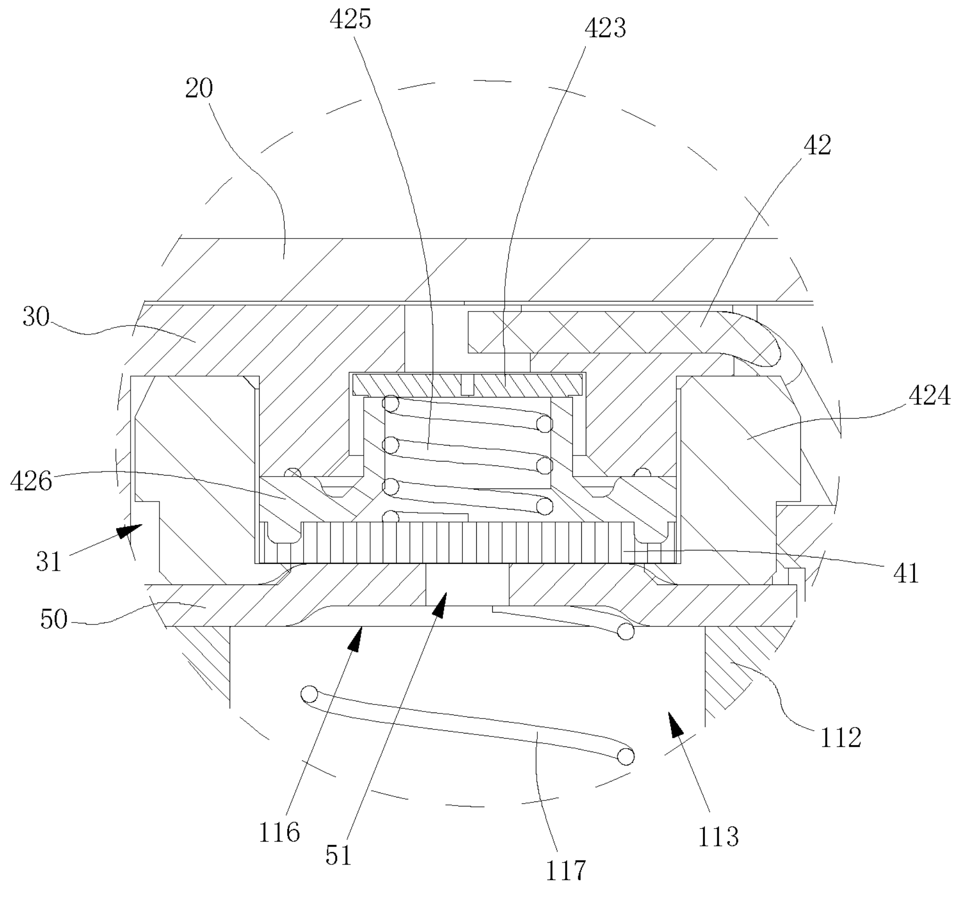
FIG. 4 illustrates an enlarged view of a part C shown in FIG. 2.
Figure 5:
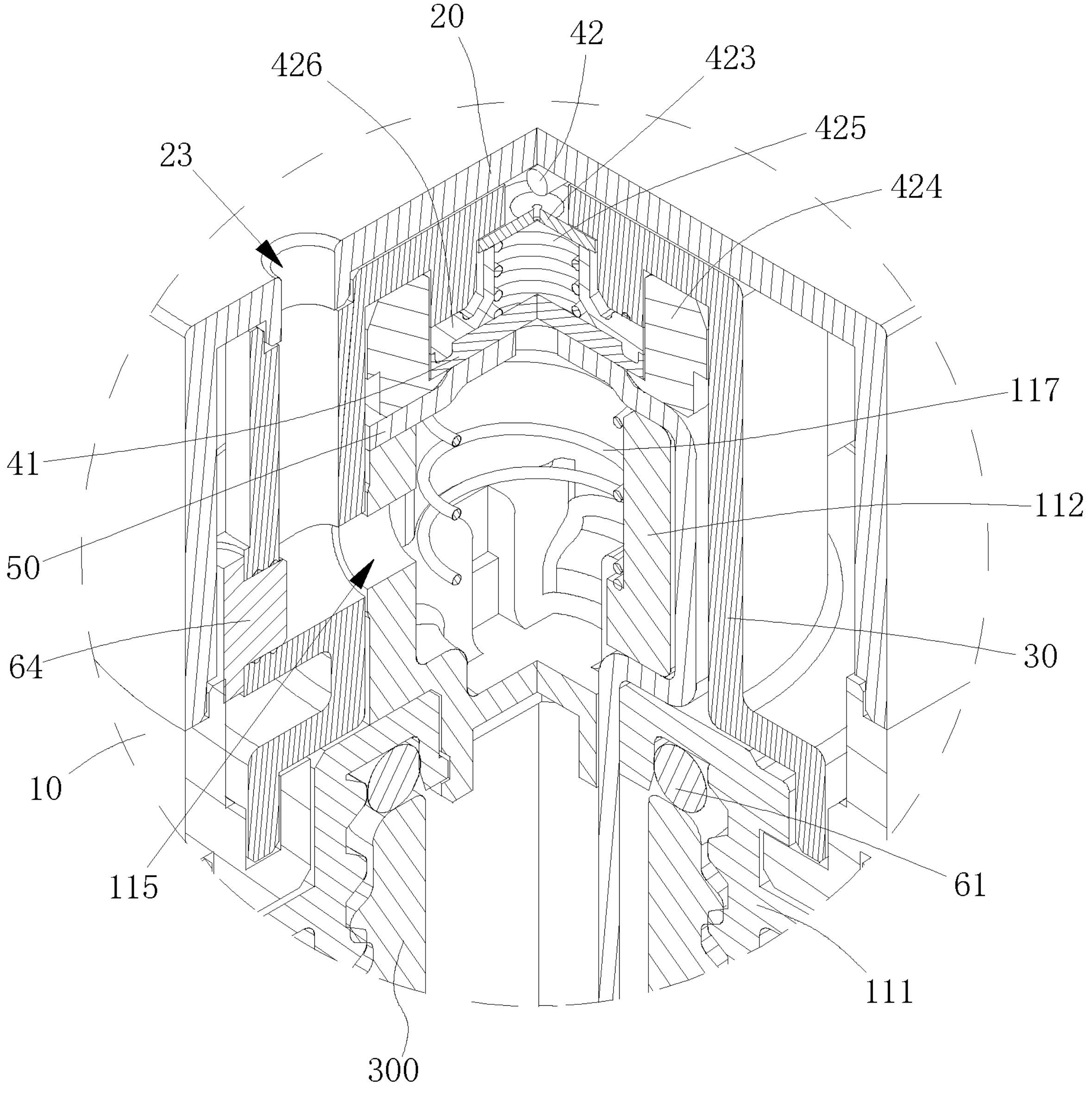
FIG. 5 illustrates an enlarged view of a part D shown in FIG. 3.
Figure 6:
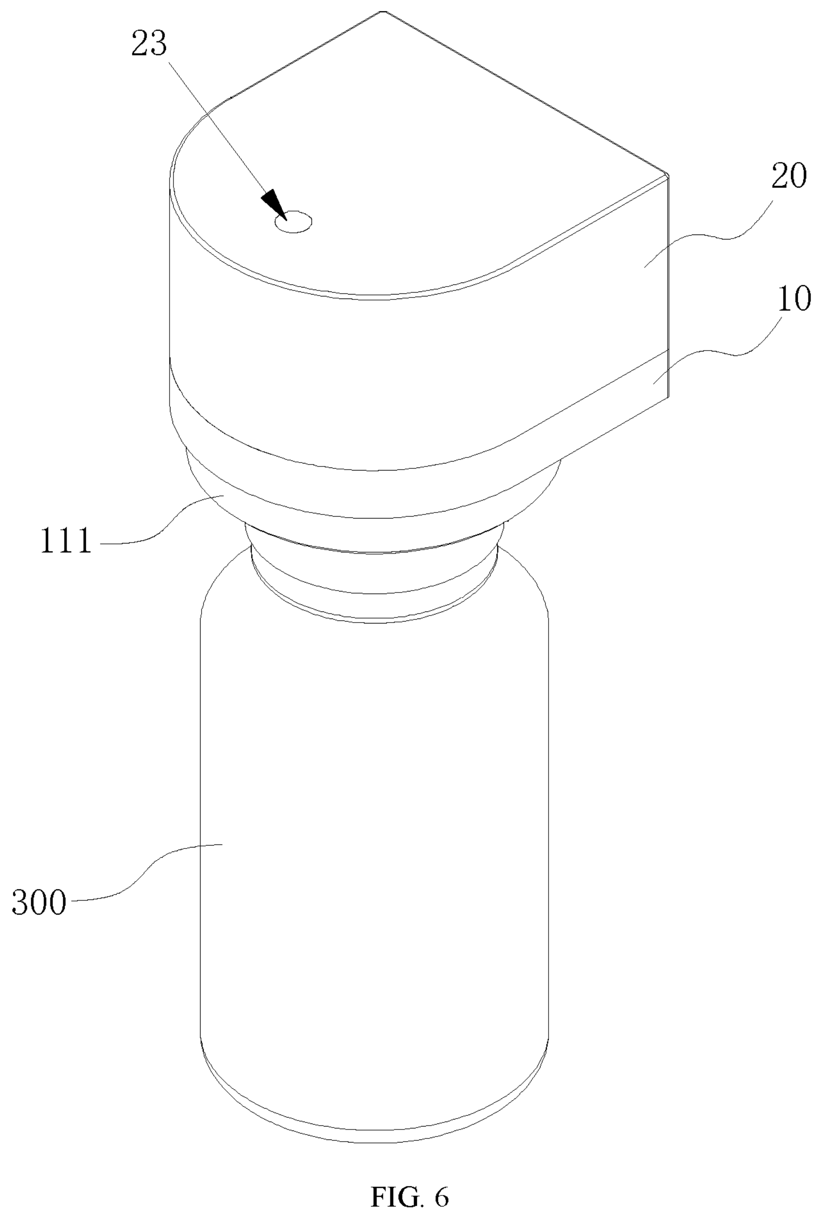
FIG. 6 illustrates a first schematic assembly diagram of an atomizer head and an essential oil bottle in the aromatherapy atomizer according to the first embodiment of the present application.
Figure 7:
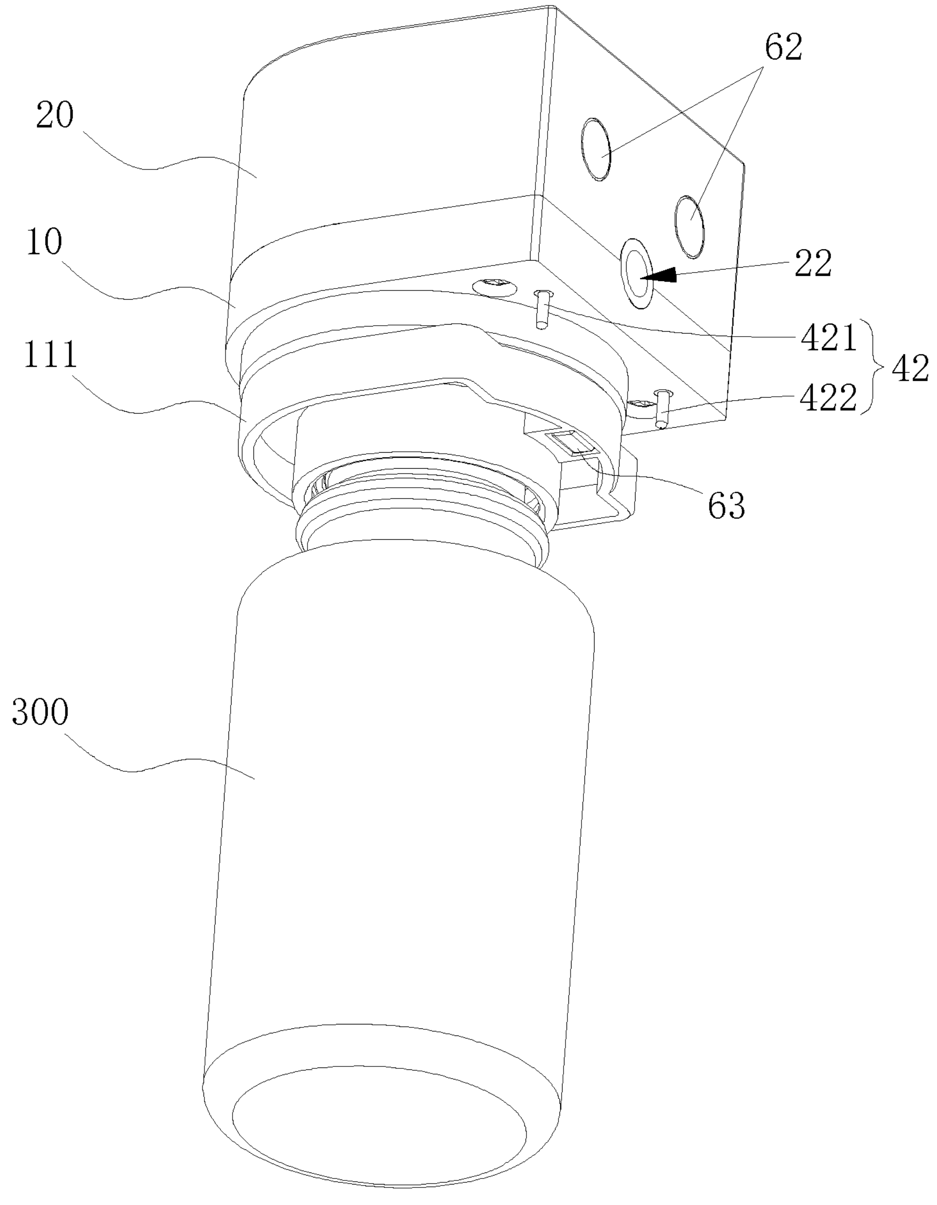
FIG. 7 illustrates a second schematic assembly diagram of the atomizer head and the essential oil bottle in the aromatherapy atomizer according to the first embodiment of the present application.

As shown in FIGS. 7 to 9, the atomization structure further includes a terminal assembly 42 electrically connected with the ceramic atomization plate 41. The terminal assembly 42 includes a first terminal 421, a second terminal 422 (the present application are described by taking the first terminal 421 as the positive terminal and taking the second terminal 422 as the negative terminal as an example below). More particularly, the atomization structure further includes a terminal adapter 423 and a terminal heat dissipation member 424. One end of the positive terminal is electrically connected with the terminal adapter 423, and the other end of the positive terminal pierces through the bottom shell 10. In this condition, the terminal adapter 423 serves as a positive electrode conductive part and is configured to be electrically connected to a positive electrode of the ceramic atomization plate 41, one end of the second terminal 422 is electrically connected with the terminal heat dissipation member 424, and the other end of the second terminal 422 pierces through the bottom shell 10. In this condition, the terminal heat dissipation member 423 serves as a negative electrode conductive part and is configured to be electrically connected to a positive electrode of the ceramic atomization plate 41. Moreover, the terminal heat dissipation member 424 encloses and supports the ceramic atomization plate 41. That is, the terminal adapter 423 and the terminal heat dissipation member 424 are electrically connected with the ceramic atomization plate 41, respectively. Moreover, the ceramic atomization plate 41, the terminal adapter 423 and the terminal heat dissipation member 424 are mounted on the support structure 30. When the ceramic atomization plate 41 is in operation, the ceramic atomization plate 41 generates a large amount of heat. If the heat from the ceramic atomization plate 41 is not dissipated timely, the ceramic atomization plate 41 may be damaged, what's worse, the high temperature may damage other components inside the atomizer head 100. Furthermore, the ceramic atomization plate 41 with high temperature will cause an extremely high temperature of the essential oil contacting the ceramic atomization plate 41, so that a peculiar smell is produced. Thus, in this embodiment of the present application, the terminal heat dissipation member 424 is used to be conductive with the ceramic atomization plate 41 by contacting the ceramic atomization plate 41, so that the terminal heat dissipation member 424 is also served as a heat dissipation member of the ceramic atomization plate 41, the heat generated by the ceramic atomization plate 41 is transferred and dissipated. Moreover, some heat of the ceramic atomization plate 41 may also be taken away in a process of atomizing the essential oil sucked up by the flexible wick 50 abutting against the ceramic atomization plate 41 into vapor, so that the temperature of the ceramic atomization plate 41 is always not too high, and the service life and the reliability of the ceramic atomization plate 41 are ensured. In order to ensure that the first terminal 421 and the second terminal 422 are always in a stable electrical connection with the ceramic atomization plate 41, and in order to avoid the first terminal 421 from being fixed on the ceramic atomization plate 41 through tin solder, thereby affecting high frequency oscillation of the ceramic atomization plate 41, as shown in FIG. 4, FIG. 5 and FIG. 9, the terminal assembly 42 further includes a conductive spring 425, one end of the conductive spring 425 abuts against the ceramic atomization plate 41, the other end of the conductive spring 425 abuts against the terminal adapter 423. After assembling, the conductive spring 425 generates elastic forces against the ceramic atomization plate 41 and the terminal adapter 423 respectively, so that a stable assembly between the first terminal 421 and the ceramic atomization plate 41 is ensured. Moreover, due to the elastic force generated by the conductive spring 425 against the ceramic atomization plate 41, the ceramic atomization plate 41 is pressed against the terminal heat dissipation member 424 to achieve an electrical connection between the ceramic atomization plate 41 and the terminal heat dissipation member 424, so that a stable assembly between the second terminal 422 and the ceramic atomization plate 41 is ensured.

Furthermore, in order to ensure an effective insulation between the terminal adapter 423 and the terminal heat dissipation member 424 and avoid a short circuit, as shown in FIG. 4, FIG. 5 and FIG. 9, the terminal assembly 42 further includes a silicone sleeve 426. One end of the silicone sleeve 426 abuts against the ceramic atomization plate 41, the other end of the silicone sleeve 426 abuts against the terminal adapter 423, and the silicone sleeve 426 is sleeved on the conductive spring 425.

As shown in FIGS. 1 to 3, FIG. 11 and FIG. 12, the aromatherapy atomizer according to the first embodiment of the present application includes a housing 201, a battery 202, a circuit board 203, a contact member 204 and the aforesaid innovatively designed atomizer head 100.

In particular, the housing 201 is provided with a mounting space 211 and an accommodation compartment 212, the accommodation compartment 212 is configured to accommodate the essential oil bottle 300, the bottom shell 10 and the housing 201 are detachably connected, both the battery 202 and the circuit board 203 are arranged in the mounting space 211, the battery 202 is electrically connected with the circuit board 203, the contact member 204 is electrically connected with the circuit board 203, the contact member 204 penetrates through the mounting space 211. The contact member 204 is configured to abut against and be conductive with the first terminal 421 and the second terminal 422 of the terminal assembly 42 when the essential oil bottle 300 is inserted into the accommodation compartment 212. The battery 202 is used to provide electrical energy, the battery 202 may be a dry cell or a storage battery, and is preferably a rechargeable lithium-ion battery.

By applying the aromatherapy atomizer provided by this embodiment of the present application, in an atomization process, the essential oil bottle 300 is inserted into the accommodation compartment 212, in this condition, the terminal assembly 42 is in conduction with the contact member 204, so that the battery 202 provides electrical energy, which makes the ceramic atomization plate 41 to be oscillated; moreover, the flexible wick 50 sucks out the liquid in the essential oil bottle 300 and transfers the liquid to the part of the flexible wick 50 abutting against the ceramic atomization plate 41, the liquid is atomized due to the oscillation of the ceramic atomization plate 41, then, the atomized vapor is sprayed into the cavity 31 from the spray through-hole 51 and is diffused into the air through the air outlet 22.

Furthermore, an arrangement of contact conduction between the terminal assembly 42 and the contact member 204 is used in the aromatherapy atomizer according to this embodiment of the present application, so that the atomizer head 100 can be quickly disassembled from the housing 201, and then is replaced with a new essential oil bottle 300 having different fragrance, the user's requirement of quickly replacing essential oil bottles 300 having different fragrances is satisfied.

Figure 2:
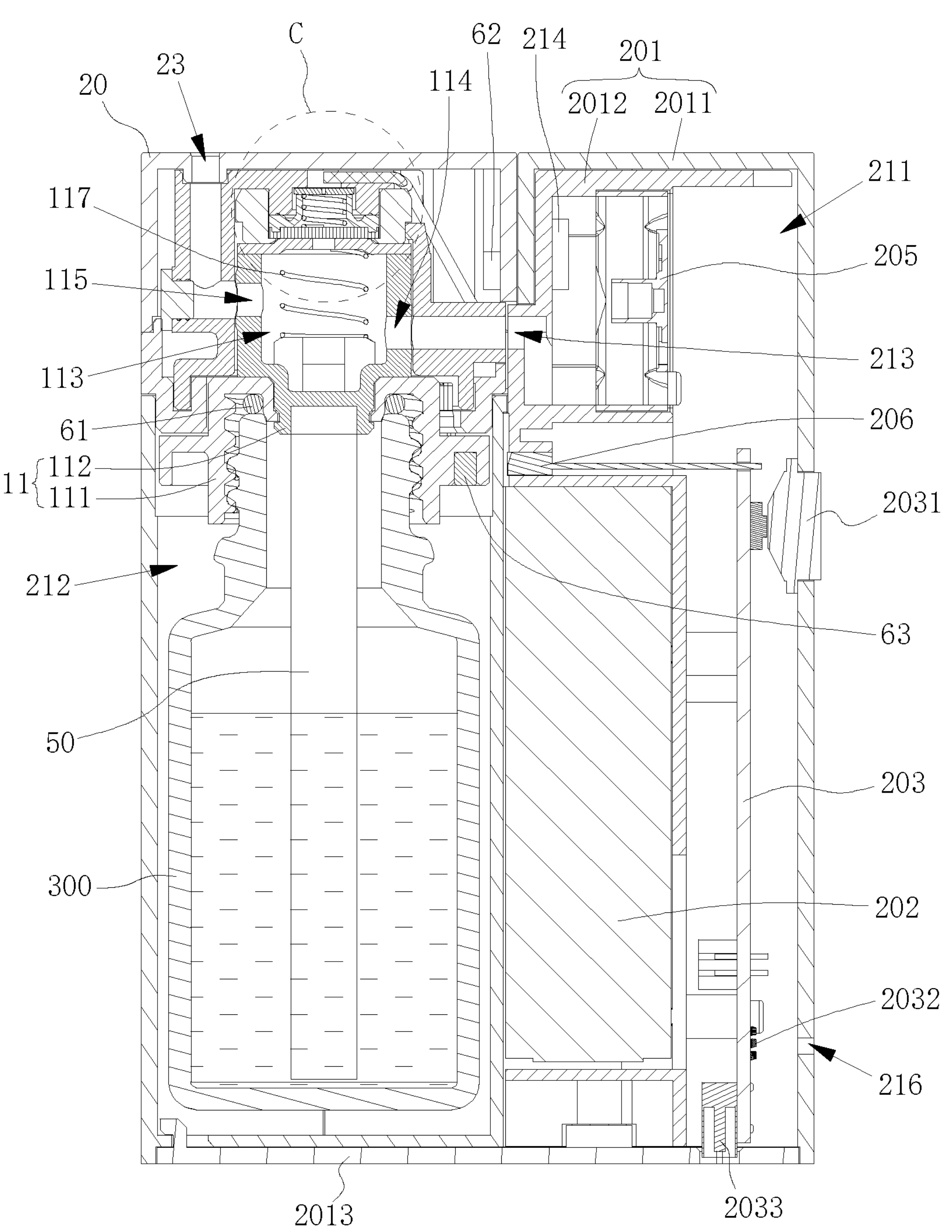
FIG. 2 illustrates a sectional view of the aromatherapy atomizer along a A-A direction, as shown in FIG. 1.
Figure 3:
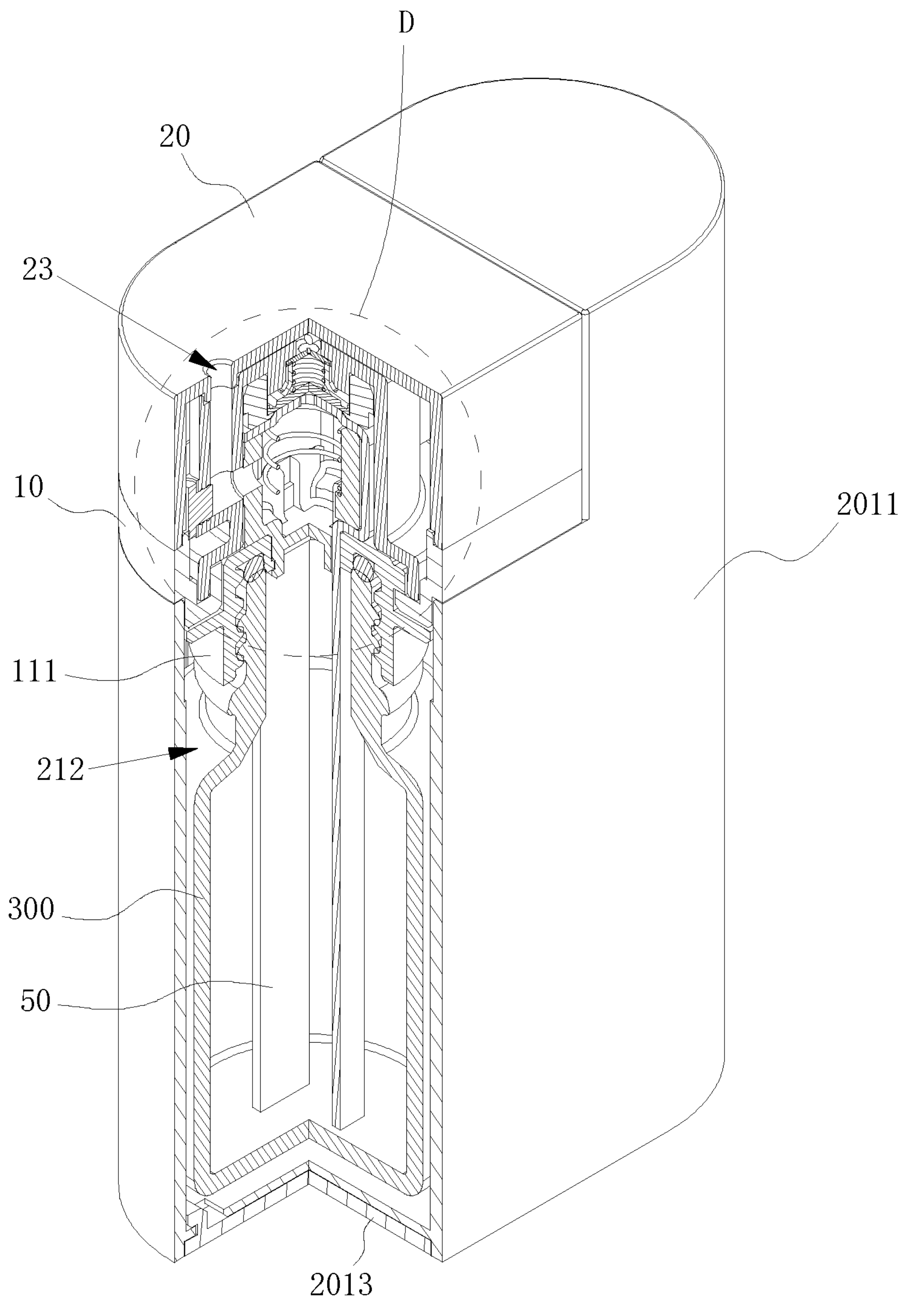
FIG. 3 illustrates a sectional view of the aromatherapy atomizer along a A-B direction, as shown in FIG. 1.
Figure 12:
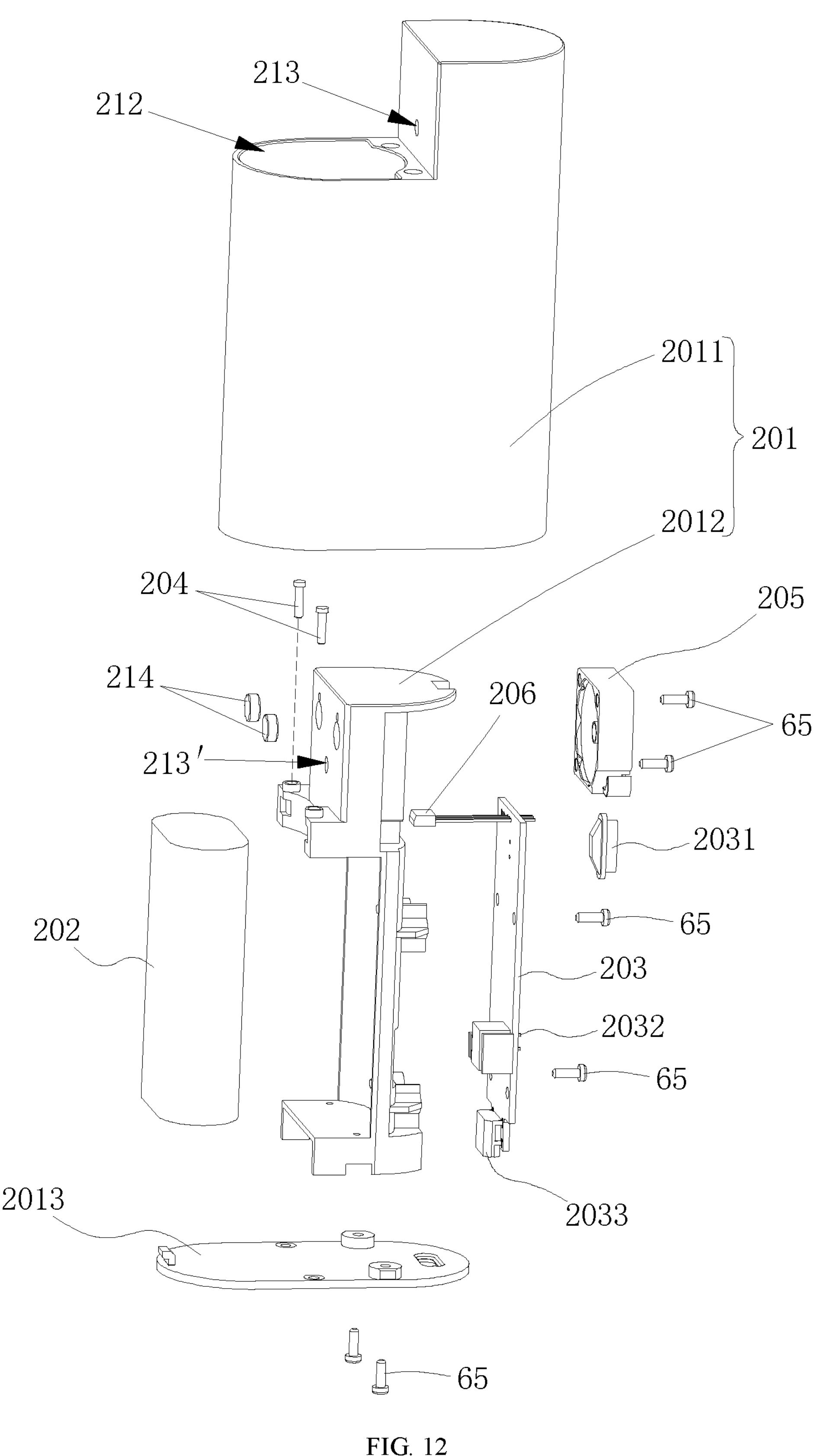
FIG. 12 illustrates a schematic exploded view of the aromatherapy atomizer as shown in FIG. 11.
Figure 13:
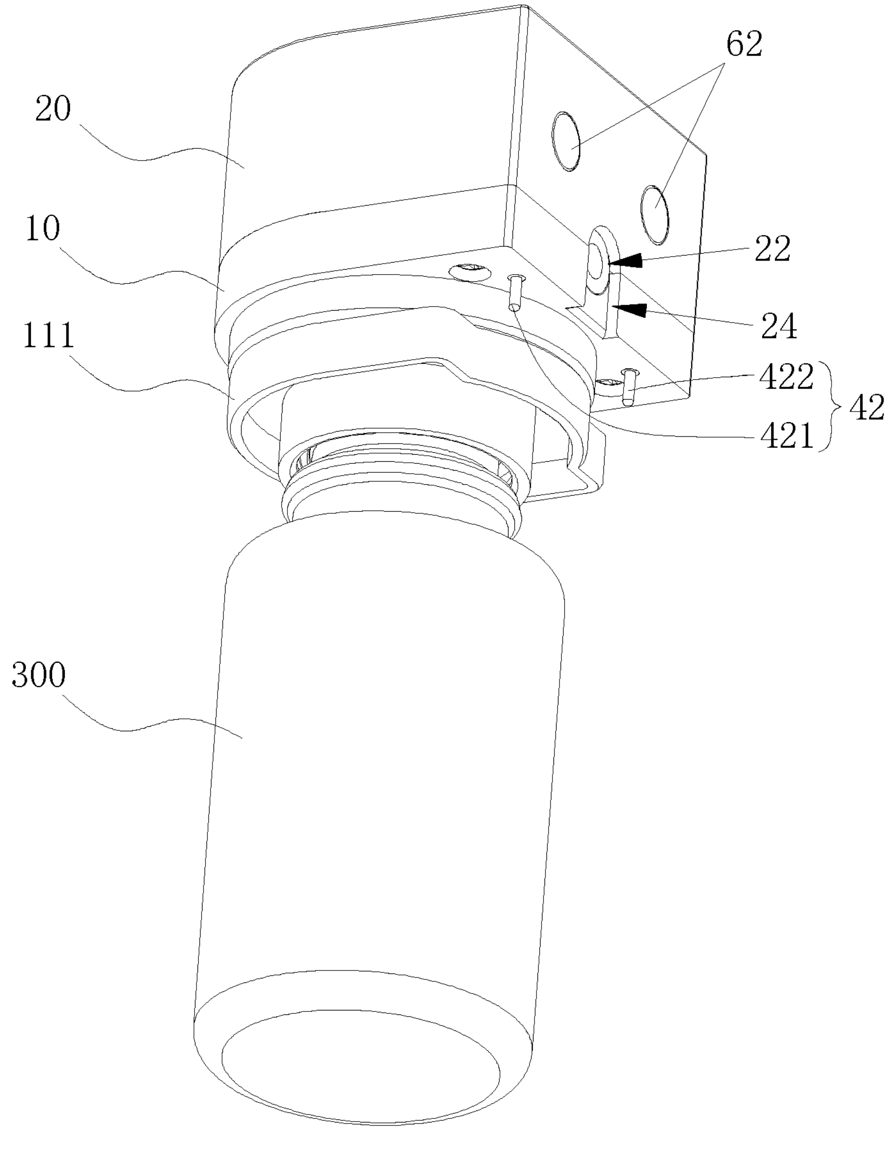
FIG. 13 illustrates a schematic assembly diagram of an atomizer head and an essential oil bottle in an aromatherapy atomizer according to a second embodiment of the present application.
Figure 14:
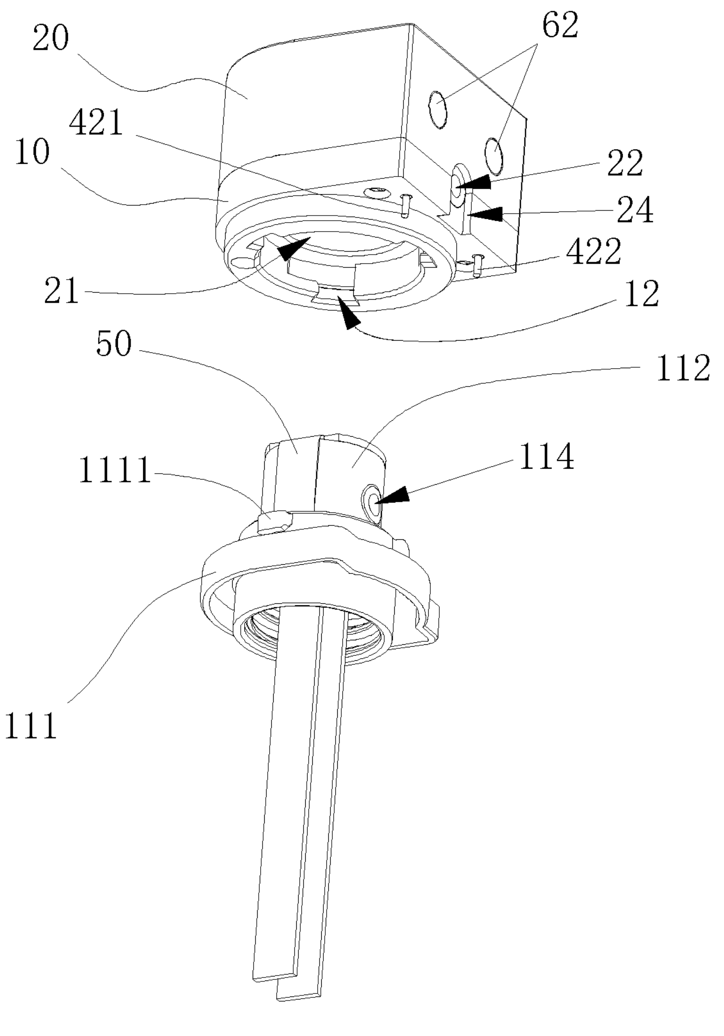
FIG. 14 illustrates an exploded view of the atomizer head and the essential oil bottle as shown in FIG. 13.
Figure 14:
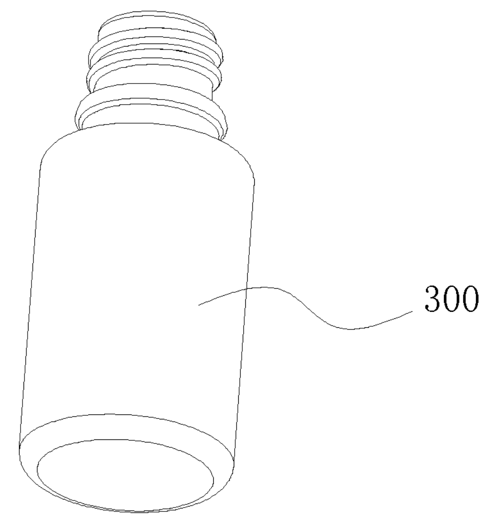
Figure 15:
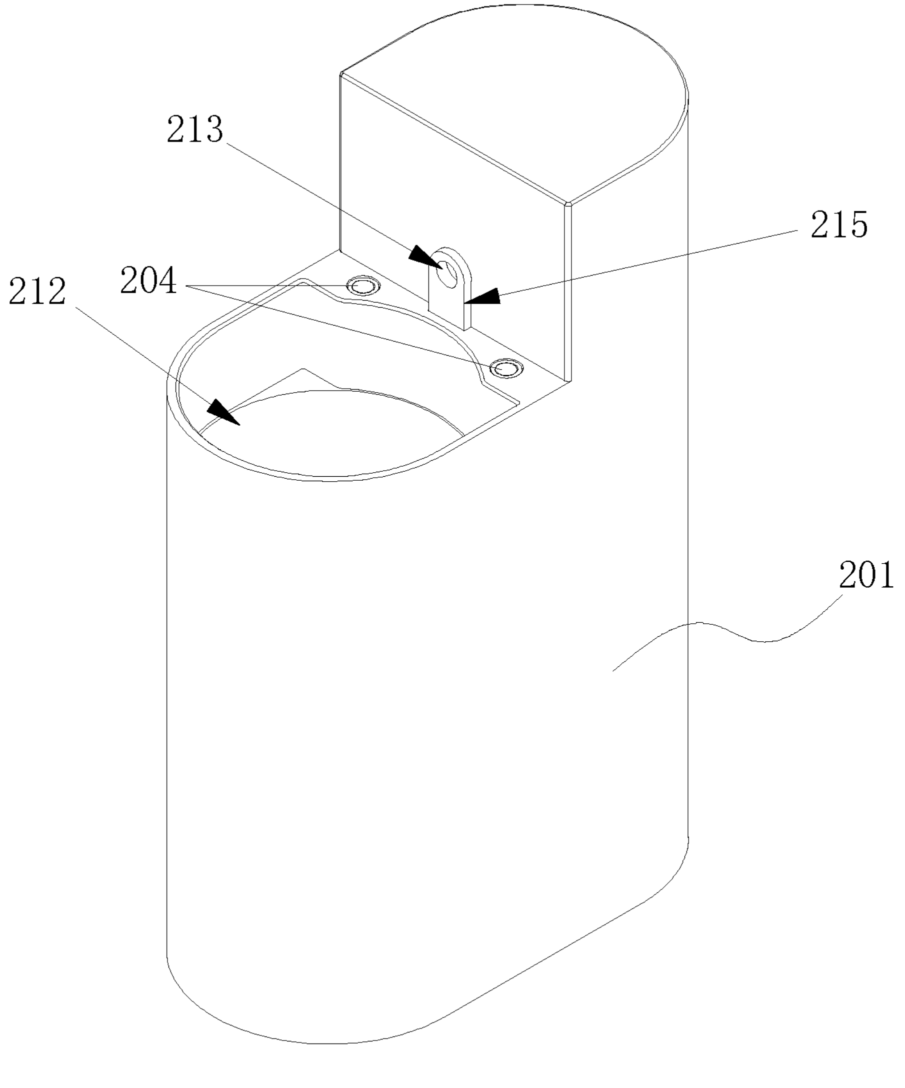
FIG. 15 illustrates a schematic assembly diagram of a housing, a battery, a circuit board and a contact member in the aromatherapy atomizer according to the second embodiment of the present application.
Figure 16:
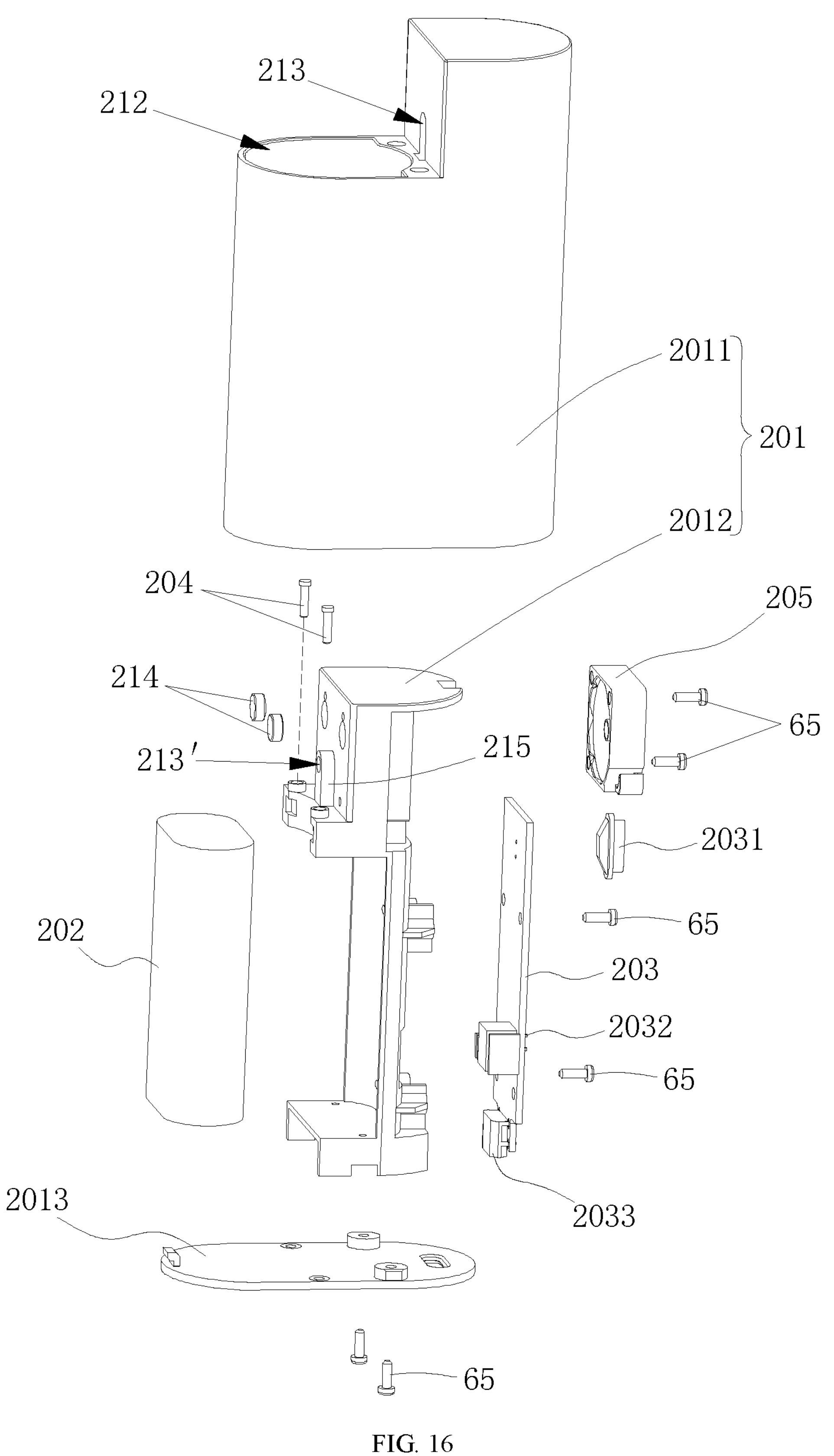
FIG. 16 illustrates a schematic assembly diagram of the aromatherapy atomizer as shown in FIG. 15.

In order to be able to diffuse the vapor generated by atomization into the air more quickly, therefore, as shown in FIG. 2 and FIG. 12, the aromatherapy atomizer further includes a fan 205 mounted in the mounting space 211, the fan 205 is electrically connected with the circuit board 203, the housing 201 is provided with an gas outlet 213, the fan 205 is arranged to be opposite to the gas outlet 213. Correspondingly, the bottom shell 10 or the shell cover 20 is further provided with the air inlet 22, the gas outlet 213 is communicated with the air inlet 22 when the essential oil bottle 300 is inserted into the accommodation compartment 212. Airflow is blown through the fan 205, and the airflow is utilized to carry the vapor generated by atomization out of the air outlet 22, so that the vapor is diffused into the air more quickly.

In the first embodiment of the present application, the housing 201 includes the outer shell 2011, a shell holder 2012 and a bottom sealing plate 2013. As shown in FIG. 12, the mounting space 211 and the accommodation compartment 212 are formed by the housing 2011, the battery 202 is mounted on the shell holder 2012, the circuit board 203 is arranged on the shell holder 2012 by screws 65, the fan 205 is arranged on the shell holder 2012 by screws 65, either. Due to this arrangement, the shell holder 2012, the battery 202, the circuit board 203 and fan 205 are taken a whole component that is placed into the mounting space 211. Then, the bottom sealing plate 2013 is arranged at an inlet of the mounting space 211 and is locked by screws 65. Furthermore, a part of the shell holder 2012 corresponding to the fan 205 is provided with an air vent 213', and the housing 2011 is provided with an gas outlet 213 corresponding to the air vent 213'.

As shown in FIG. 2 and FIGS. 7 to 9, a limiting magnet 62 is mounted on the shell cover 20, the limiting magnet 62 is used to block the atomizer head 100 from being disengaged from the housing 201 when the atomizer head 100 is arranged in the housing 201. Accordingly, as shown in FIG. 2 and FIG. 12, an adsorption magnet 214 is mounted in the housing 201, and is used to be magnetically connected with the limiting magnet 62 of the atomizer head 100 when the essential oil bottle 300 is inserted into the accommodation compartment 212, so that the atomizer head 100 can be blocked from being disengaged from the housing 201. Due to this arrangement, when the atomizer head 100 and the essential oil bottle 300 are properly mounted into the housing 201 by the user, the limiting magnet 62 and the adsorption magnet 214 are magnetized with each other, thereby securing the atomizer head 100 on the housing 201 stably. Moreover, the essential oil bottle 300 is inserted into the accommodation compartment 212, and is fixedly arranged, so that the stability of the atomizer head 100 is ensured.

As shown in FIGS. 2 and 7 to 9, the connection part 11 is provided with a detection magnet 63, and the detection magnet 63 is used to detect whether the atomizer head 100 is mounted in place when the atomizer head 100 is mounted in the housing 201. Accordingly, as shown in FIG. 2 and FIG. 12, the aromatherapy atomizer further includes a Hall sensor 206, the Hall sensor 206 is mounted in the housing 201, and is electrically connected to the circuit board 203, and the Hall sensor 206 is used to detect whether the detection magnet 63 of the atomizer head 100 is mounted in place relative to the housing 201 when the essential oil bottle 300 is inserted into the accommodation compartment 212. In this way, when the atomizer head 100 and the essential oil bottle 300 are properly mounted in the housing 201 by the user, the Hall sensor 206 detects that the atomizer head 100 has been mounted in place. When a switch button 2031 is activated by the user, the Hall sensor 206 controls the terminal assembly 42 to be conductive normally through the circuit board 203, so that the atomization of the essential oil is performed normally. When the atomizer head 100 is not mounted in place, when the switch button 2031 is activated by the user, the Hall sensor 206 sends out a warning prompt through the circuit board 203. At this time, the user may adjust the mounting position of the atomizer head 100 until the atomizer head 100 is properly mounted.

As shown in FIG. 1 and FIG. 2, the housing 2011 is provided with a light hole 216. Furthermore, as shown in FIG. 2 and FIG. 12, the circuit board 203 is provided with an indicator light 2032, the indicator light 2032 emits light and transmits light through the light hole 216. The circuit board 203 is further provided with a charging connector 2033, when the charging connector 2033 is used to charge the battery 202, the indicator light 2032 emits light. For example, the indicator light 2032 emits a constant red light to indicate that the battery 202 is being charged, the indicator light 2032 emits a constant green light to indicate that the battery 202 has been fully charged. In addition, when the atomizer head 100 is not mounted in place, when the user activates the switch button 2031, Hall sensor 206 sends out the warning prompt through the circuit board 203, that is, the indicator light 2032 is tuned on, the indicator light 2032 is operated such as in a form of breathing light or flashing.

Second Embodiment

As shown in FIGS. 13-16, FIGS. 13-16 illustrate a schematic structural diagram of an aromatherapy atomizer according to a second embodiment of the present application.

In the second embodiment of the present application, the housing 201 is provided with a positioning projection 215, the gas outlet 213 is formed on the positioning projection 215, the shell cover 20 is provided with a positioning groove 24, the air inlet 22 is formed on the bottom of the positioning groove 24, the positioning projection 215 is embedded in the positioning groove 24 when the essential oil bottle 300 is inserted into the accommodation compartment 212, and the gas outlet 213 is communicated with the air inlet 22. The atomizer head 100 and the essential oil bottle 300 are mounted in the housing 201 by the user, a quick positioning of the atomizer head 100 is achieved through the matching between the positioning projection 215 and the positioning groove 24, so that the atomizer head 100 can be quickly and properly mounted.

In other words, the aromatherapy atomizer according to the second embodiment of the present application is not provided with the detection magnet 63 and the Hall sensor 206, the atomizer head 100 is fixed on the housing 201 merely through a mechanical mating between the positioning projection 215 and the positioning groove 24.

When the second embodiment is compared with the first embodiment, the aromatherapy atomizer in the second embodiment and the aromatherapy atomizer in the first embodiment have the same structure in addition to the aforesaid structures of the positioning projection 215 and the positioning groove 24 described in the second embodiment, so that the structure of the aromatherapy atomizer in the second embodiment is not repeatedly described here.

Third Embodiment

Figure 17:
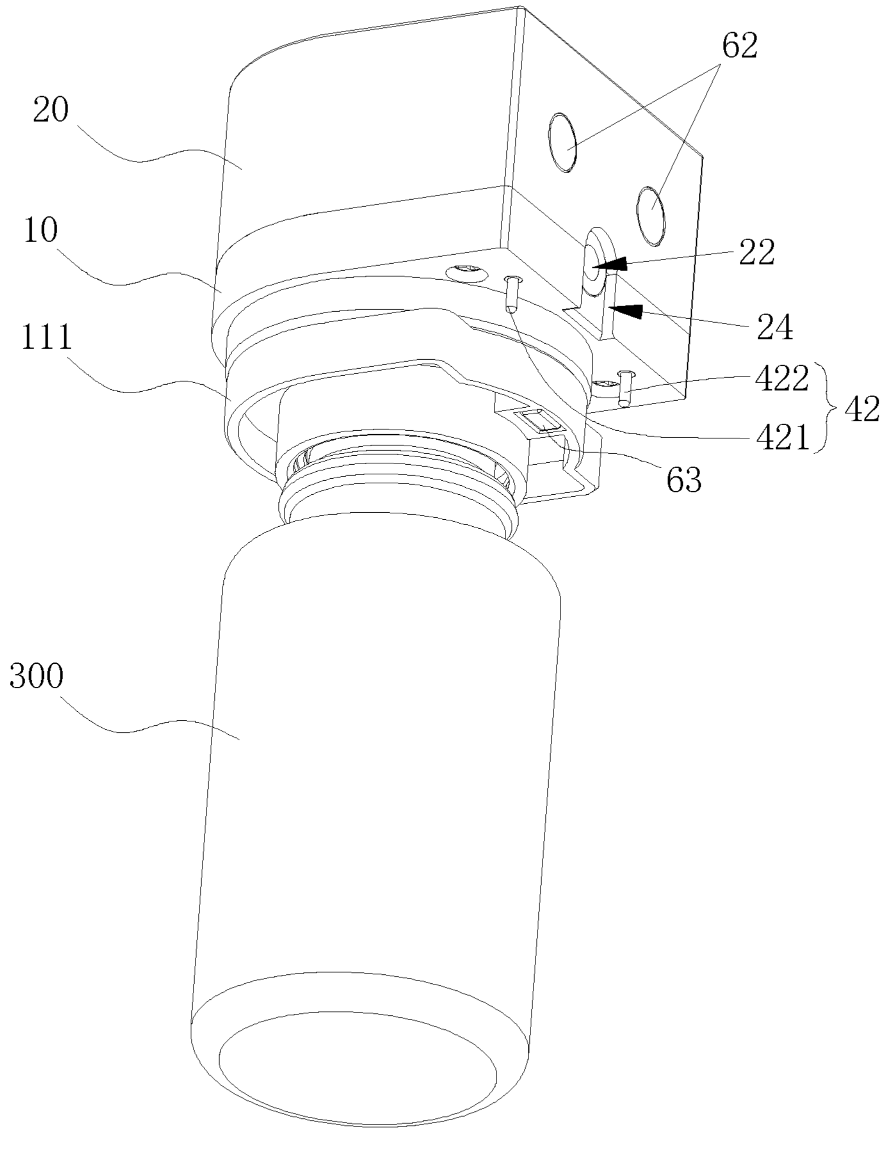
FIG. 17 illustrates a schematic assembly diagram of an atomizer head and an essential oil bottle in an aromatherapy atomizer according to a third embodiment of the present application.
Figure 18:
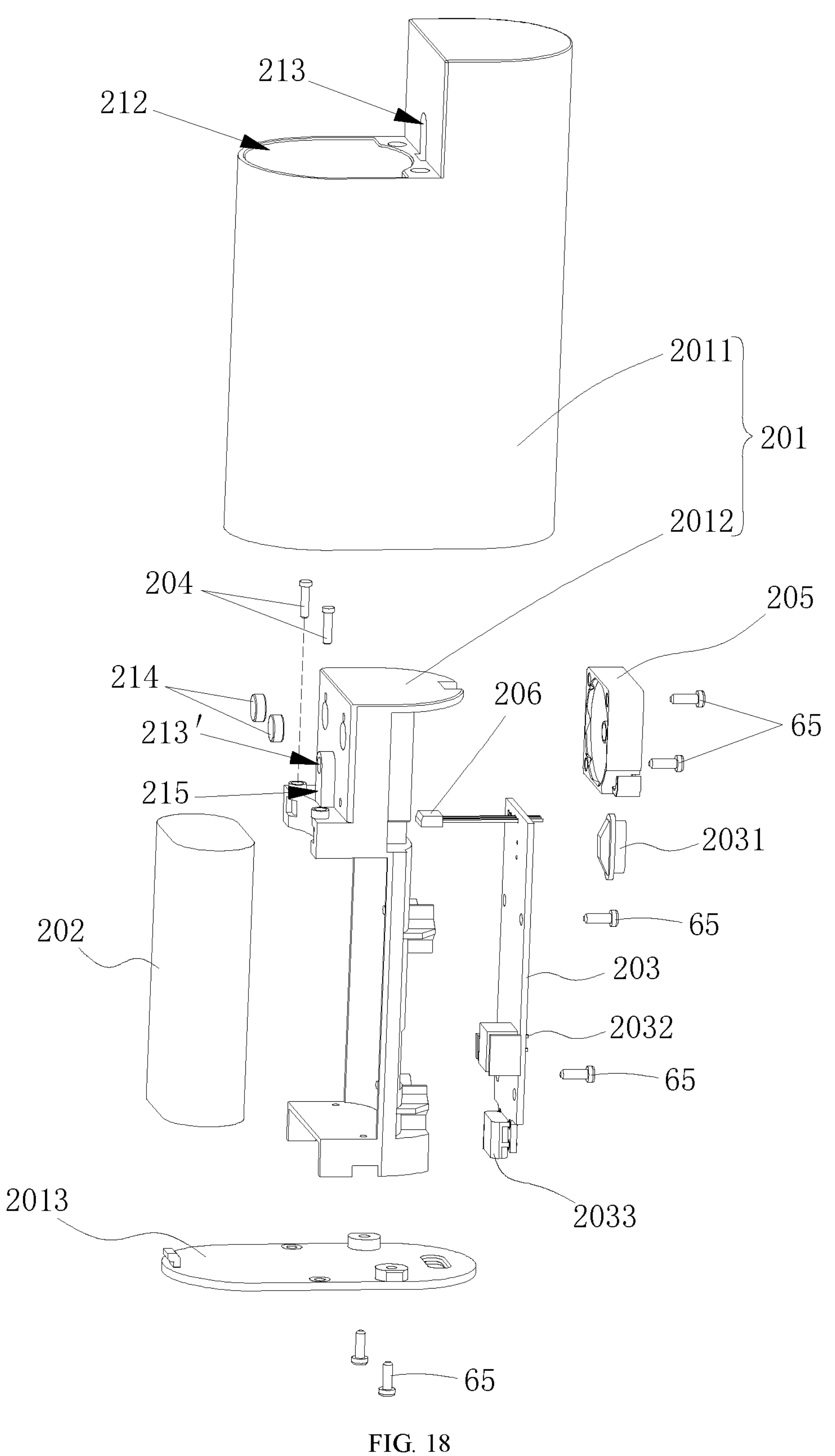
FIG. 18 illustrates a schematic assembly diagram of a housing, a battery, a circuit board and a contact member in the aromatherapy atomizer according to the third embodiment of the present application.

As shown in FIG. 17 and FIG. 18, FIG. 17 and FIG. 18 illustrate a schematic structural diagram of an aromatherapy atomizer according to a third embodiment of the present application.

In the third embodiment of the present application, not only the detection magnet 63 and the Hall sensor 206 are used in cooperation to detect whether the atomizer head 100 has been properly mounted in the housing 201, the positioning and the mounting of the atomizer head 100 can also be realized through the matching between the positioning projection 215 and the positioning groove 24, so that the atomizer head 100 can be quickly and properly mounted. As a matter of fact, the third embodiment is a combination of the first embodiment and the second embodiment.

When the third embodiment is compared with the first embodiment or the second embodiment, the aromatherapy atomizer in the third embodiment, the aromatherapy atomizer in the first embodiment and the aromatherapy atomizer in the third embodiment have the same structure in addition to the aforesaid structures described in the third embodiment, so that the structure of the aromatherapy atomizer in the third embodiment is not repeatedly described here.

Fourth Embodiment

In the aromatherapy atomizer (not shown) according to the fourth embodiment of the present application, the battery 202, the circuit board 203, and the fan 205 are mounted in the accommodation space 21, and the battery 202 is electrically connected with the circuit board 203, both the first terminal 421 and the second terminal 422 are electrically connected with the circuit board 203, and the fan 205 is electrically connected with the circuit board 203. The support frame 112 is provided with a gas inlet 114 connected with the atomization chamber 113, and the gas inlet 114 is arranged to be opposite to the fan 205 when the support frame 112 penetrates through the insertion hole and is inserted into the accommodation space 21. Due to this arrangement, the various electronic components of the aromatherapy atomizer are integrated and assembled in the accommodation space 21. The housing 201 is only provided with the accommodation compartment 212 for accommodating the essential oil bottle 300.

In the aromatherapy atomizer according to the fourth embodiment, inlet airflow required by the fan 205 can flow through the gap after the bottom shell 10 and the shell cover 20 are covered with each other, and enter the accommodation space 21, and then is blown into the gas inlet 114 through the fan 205, and take the vapor in the atomization chamber 113, and flow in a direction from the outlet hole 115 to the air outlet 23, and is finally diffused into the air.

When the fourth embodiment is compared with the first embodiment or the second embodiment or the third embodiment, the aromatherapy atomizer in the fourth embodiment, the aromatherapy atomizer in the first embodiment, the aromatherapy atomizer in the second embodiment and the aromatherapy atomizer in the third embodiment have the same structure in addition to the aforesaid structures described in the fourth embodiment, so that the structure of the aromatherapy atomizer in the fourth embodiment is not repeatedly described here.

Some selectable embodiments of the present application are only described in the foregoing specification, and these selectable embodiments are not intended to limit the present application. It is obvious to the person of ordinary skill in the art that, various modifications and changes may be made to the present application. Any modification, equivalent replacement, improvement, and the like, which are made within the spirit and the principle of the present application, should all be included in the protection scope of the claims of the present application.

What is claimed is:

1. A detachable essential oil atomizer head, comprising:

a bottom shell, a shell cover, a connection part and an atomization structure, wherein the shell cover is detachably coupled to the bottom shell and encloses the bottom shell to form an accommodation space, the shell cover is provided with an air outlet connected to the accommodation space; an essential oil bottle is mounted at one side of the connection part, the other side of the connection part away from the essential oil bottle is detachably connected to the bottom shell; the bottom shell is provided with an insertion hole connected to the accommodation space;

the atomization structure comprises a ceramic atomization plate and a flexible wick, wherein the ceramic atomization plate is mounted in the accommodation space, one end of the flexible wick is arranged on one side of the connection part away from the essential oil bottle and abuts against the ceramic atomization plate, an other end of the flexible wick penetrates through the connection part and is extended into the essential oil bottle, and the flexible wick is provided with at least one spray-through hole;

wherein the connection part comprises a connection body and a support frame, the support frame is provided with an atomization chamber, an outlet hole and an aperture, both the outlet hole and the aperture are connected to the atomization chamber; the support frame is arranged to be inserted in the connection body, the flexible wick encloses the support frame so as to cover the aperture and is not connected to the outlet hole, the flexible wick is arranged to penetrate through the support frame and the connection body and extend into the essential oil bottle, the support frame penetrates through the insertion hole and is inserted into the accommodation space, such that a part of the flexible wick corresponding to the aperture abuts against the ceramic atomization plate, and the outlet hole is connected to the air outlet; wherein the connection body is detachably connected with the bottom shell;

the connecting part further comprises a support spring assembled in the atomization chamber, one end of the support spring is arranged in an inner wall of the atomization chamber, an other end of the support spring penetrates through the aperture and is pressed against the flexible wick.

2. The detachable essential oil atomizer head according to claim 1, wherein, a middle portion of the flexible wick abutting against the ceramic atomization plate is provided with the at least one spray through-hole, the at least one spray through-hole has an aperture, and a diameter of the aperture ranges from 0.5 mm to 5 mm.

3. The detachable essential oil atomizer head according to claim 1, further comprising a support structure fixedly mounted in the accommodation space, the support structure is provided with a cavity connected to the air outlet.

4. The detachable essential oil atomizer head according to claim 3, wherein, the atomization structure further comprises a terminal assembly, a terminal adapter, a terminal heat dissipation member and a conductive spring, wherein the terminal assembly comprises a first terminal and a second terminal, both the terminal adapter and the terminal heat dissipation member are mounted in the support structure; one end of the conductive spring is electrically connected with the terminal adapter, an other end of the conductive spring abuts against the ceramic atomization plate to enable the ceramic atomization plate to be conductive; the terminal heat dissipation member encloses and supports the ceramic atomization plate, and the terminal heat dissipation member is electrically connected with the ceramic atomization plate; the first terminal is electrically connected to the terminal adapter, the second terminal is electrically connected with the terminal heat dissipation member, and the first terminal and the second terminal are configured to be electrically connected to a power supply.

5. The detachable essential oil atomizer head according to claim 4, wherein, the atomization structure further comprises a silicone sleeve, one end of the silicone sleeve abuts against the ceramic atomization plate, an other end of the silicone sleeve abuts against the terminal adapter, and the silicone sleeve is sleeved on the conductive spring.

6. The detachable essential oil atomizer head according to claim 4, wherein, the connection part further comprises a sealing gasket, the sealing gasket is configured to form a sealing between the connection body and a bottle mouth of the essential oil bottle when the connection part is connected with the essential oil bottle.

7. An aromatherapy atomizer, comprising:

a detachable essential oil atomizer, comprising:

a bottom shell, a shell cover, a connection part and an atomization structure, wherein the shell cover is detachably coupled to the bottom shell and encloses the bottom shell to form an accommodation space, the shell cover is provided with an air outlet connected to the accommodation space, an essential oil bottle is mounted at one side of the connection part, an other side of the connection part away from the essential oil bottle is detachably connected to the bottom shell; the bottom shell is provided with an insertion hole connected to the accommodation space; the atomization structure comprises a ceramic atomization plate and a flexible wick, wherein the ceramic atomization plate is mounted in the accommodation space, one end of the flexible wick is arranged on one side of the connection part away from the essential oil bottle and abuts against the ceramic atomization plate, an other end of the flexible wick penetrates through the connection part and is extended into the essential oil bottle, and the flexible wick is provided with at least one spray-through hole;

wherein the connection part comprises a connection body and a support frame, the support frame is provided with an atomization chamber, an outlet hole and an aperture, both the outlet hole and the aperture are connected to the atomization chamber; the support frame is arranged to be inserted in the connection body, the flexible wick encloses the support frame so as to cover the aperture and is not connected to the outlet hole, and the flexible wick is arranged to penetrate through the support frame and the connection body and extend into the essential oil bottle, the support frame penetrates through the insertion hole and is inserted into the accommodation space, such that a part of the flexible wick corresponding to the aperture abuts against the ceramic atomization plate, and the outlet hole is connected to the air outlet; wherein the connection body is detachably connected with the bottom shell;

wherein the connecting part further comprises a support spring assembled in the atomization chamber, one end of the support spring is arranged in an inner wall of the atomization chamber, an other end of the support spring penetrates through the aperture and is pressed against the flexible wick.

8. The aromatherapy atomizer according to claim 7, wherein the bottom shell or the shell cover is further provided with a gas inlet, a support frame is further provided with an air inlet connected to an atomization chamber, the air inlet is connected to the gas inlet when the support frame penetrates through the insertion hole and is inserted into the accommodation space, and the gas inlet is connected to the air outlet when the essential oil bottle is inserted into the accommodation compartment.

9. The aromatherapy atomizer according to claim 7, further comprising:

a limiting magnet arranged in the shell cover, and an adsorption magnet arranged in the housing; wherein the adsorption magnet is configured to be magnetically connected with the limiting magnet when the essential oil bottle is inserted into the accommodation compartment.

10. The aromatherapy atomizer according to claim 7, wherein, the connection part is provided with a detection magnet, the aromatherapy atomizer further comprises a Hall sensor arranged in the mounting space and electrically connected with the circuit board; wherein the Hall sensor is configured to detect whether the detection magnet is mounted in place when the essential oil bottle is inserted into the accommodation compartment.

11. The aromatherapy atomizer according to claim 7, wherein a middle portion of the flexible wick abutting against the ceramic atomization plate is provided with the at least one spray through-hole, the at least one spray through-hole has an aperture, and a diameter of the aperture ranges from 0.5 mm to 5 mm.

12. The aromatherapy atomizer according to claim 7, further comprising a support structure, the support structure is fixedly mounted in the accommodation space; the support structure is provided with a cavity connected to the air outlet, and the atomization plate is mounted in the support structure and is located in the cavity.

13. The aromatherapy atomizer according to claim 12, wherein the atomization structure further comprises a terminal assembly, a terminal adapter, a terminal heat dissipation member and a conductive spring, wherein the terminal assembly comprises a first terminal and a second terminal, both the terminal adapter and the terminal heat dissipation member are mounted in the support structure; one end of the conductive spring is electrically connected with the terminal adapter, an other end of the conductive spring abuts against the ceramic atomization plate to enable the ceramic atomization plate to be conductive; the terminal heat dissipation member encloses and supports the ceramic atomization plate, and the terminal heat dissipation member is electrically connected with the ceramic atomization plate; the first terminal is electrically connected to the terminal adapter, the second terminal is electrically connected with the terminal heat dissipation member, and the first terminal and the second terminal are configured to be electrically connected to a power supply.

14. The aromatherapy atomizer according to claim 13, wherein the atomization structure further comprises a silicone sleeve, one end of the silicone sleeve abuts against the ceramic atomization plate, an other end of the silicone sleeve abuts against the terminal adapter, and the silicone sleeve is sleeved on the conductive spring.

* * * * *